(12) United States Patent
Yu et al.

(10) Patent No.: US 8,093,427 B2
(45) Date of Patent: Jan. 10, 2012

(54) CONSTRUCTION AND SCREENING OF SOLUTION-PHASE DERIVED LIBRARY OF FENBUFEN AND ETHACRYNIC ACID

(75) Inventors: Chung-Shan Yu, Hsinchu (TW); Yuan-Hsiao Su, Hsinchu (TW); Li-Wu Chiang, Hsinchu (TW); Chia-Rong Chen, Hsinchu (TW); Shao-Wei Chen, Hsinchu (TW); Chia-Wen Huang, Hsinchu (TW); Ho-Lien Huang, Hsinchu (TW); Yin-Cheng Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 12/797,455

(22) Filed: Jun. 9, 2010

(65) Prior Publication Data

US 2011/0306668 A1     Dec. 15, 2011

(51) Int. Cl.
*C07D 38/00*     (2006.01)
*C05C 237/00*    (2006.01)

(52) U.S. Cl. ...................................................... 564/169

(58) Field of Classification Search ........................ None
See application file for complete search history.

(56) References Cited

OTHER PUBLICATIONS

Subra et al. (Peptides, 2000, Proceedings of the European Peptide Symposium, 26th Montpellier, France, Sep. 10-15).*

Chiang, Li-Wu et al., Combining a Solution-Phase Derived Library with In-Situ Cellular Bioassay: Prompt Screening of Amide-Forming Minilibraries Using MTT Assay, Chem. Pharm. Bull., vol. 57 (7), 2009, pp. 714-718.

Rui Wang et al., Ethacrynic Acid Butyl-Ester Induces Apoptosis in Leukemia Cells through a Hydrogen Peroxide-Mediated Pathway Independent of Glutathione S-Transferase P1-1 Inhibition, Cancer Res 2007; 67: (16). Aug. 15, 2007, 7856-7864.

Guangyi Jin et al., Amide derivatives of ethacrynic acid: Synthesis and evaluation as antagonists of Wnt/b-catenin signaling and CLL cell survival, Bioorganic & Medicinal Chemistry Letters 19 (2009) 606-609.

Desheng Lu et al., Ethacrynic Acid Exhibits Selective Toxicity to Chronic Lymphocytic Leukemia Cells by Inhibition of the Wnt/b-Catenin Pathway, PLoS ONE, Dec. 2009, vol. 4, Issue 12, pp. 1-10.

Bertrand Carboni et al., Aliphatic Amino Azides as Key Building Blocks for Efficient Polyamine Syntheses, J. Org. Chem. 1993,58, 3736-3741.

Jae Wook Lee et al., An efficient and practical method for the synthesis of mono-N-protected a,v-diaminoalkanes, Tetrahedron Letters 42 (2001) 2709-2711.

Phil B. Alper et al., Metal Catalyzed Diazo Transfer for the Synthesis of Azides From Amines, Tetrahedron Letters, 1996, vol. 37, No. 34, pp. 6029-6032.

Will Bannwarth et al., Multicomponent Condensations (MCCs), Combinatorial Chemistry a Practical Approach, 2000, pp. 6-21.

* cited by examiner

*Primary Examiner* — Brandon Fetterolf
*Assistant Examiner* — Anna Pagonakis
(74) *Attorney, Agent, or Firm* — WPAT, P.C.

(57) ABSTRACT

A process for synthesizing and screening solution phase derived libraries of fenbufen and ethacrynic acid is provided in the present invention. Compounds in the present invention having cytotoxicities are useful for a variety of therapeutic applications.

9 Claims, 4 Drawing Sheets

CONSTRUCTION AND SCREENING OF SOLUTION-PHASE DERIVED LIBRARY OF FENBUFEN AND ETHACRYNIC ACID

FIELD OF THE INVENTION

The present invention is related to solution phase derived libraries of fenbufen and ethacrynic acid thereof and methods for their use.

BACKGROUND OF THE INVENTION

The library generated from solution phase remains a useful methodology in combinatorial chemistry. Above all, the approach is centered around easily synthesized compound class such as amides, sulfonamides, ureas and efficiently prepared heterocycles such as thiazoles (*Combinatorial chemistry a practical approach*. ed. By Willi Bannworth and Eduard Felder. Wiley-VCH verlag GmbH, Weinheim, 2000). For example, the recent report of a solution-phase derived library in combination with an in-situ cellular screening assay had discovered two amide analogs of fenbufen and ethacrynic acid (EA) with antitumor potencies (*Chem. Pharm. Bull.* 57(7) 714-718, 2009).

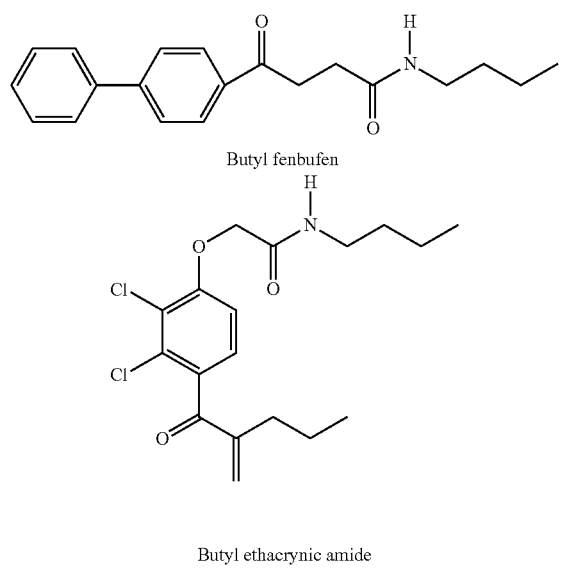

Obviously, the cytotoxicities are mainly attributed to the butyl group. The structural analysis of butyl ethacrynic amide with molecular docking (MD) showed that the butyl group lied in the deep pocket site of glutathiontransferase. MD also showed that a loose space beyond the butyl group was available for further structural modification. By contrast, a reversal orientation was adopted in the case of docking for butyl fenbufen (N-butyl-4-biphenyl-4-oxybutanamide) and cylooxygenase (COX-2). Whereas the antitumor effect of ethacynic acid butyl amide (EABA) was suggested to associate with the inhibition of glutathione S-transferase (*Cancer Res.*, 67: (16), 2007), EA butyl ester (EABE), an analog of EABA, displayed more bioactivity than EA due to its rapid entry into cells (*Bioorganic & Medicinal Chemistry Letters*, 19, 606-609, 2009).

SUMMARY OF THE INVENTION

The present invention provides a method for producing 4-azido-1-butanamine, comprising preparing TfN$_3$ and reacting TfN$_3$ with 1,4-diamine to transfer azido group by catalyst.

The present invention also provides a compound of formula:

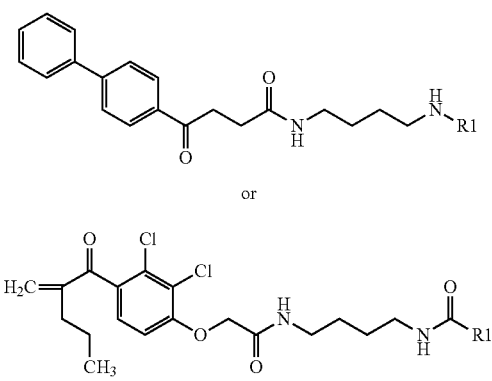

wherein the R1 represents acetyl.

The present invention further provides a method for inducing cytotoxicity in a subject comprising administering said subject the compound mentioned previously.

The present invention provides a method for inhibiting the proliferation of tumor cells comprising administering said tumor cells an inhibitory amount of the compound described above.

The present invention also provides A combinatorial library of cytotoxicity compounds comprising a plurality of compound of formula:

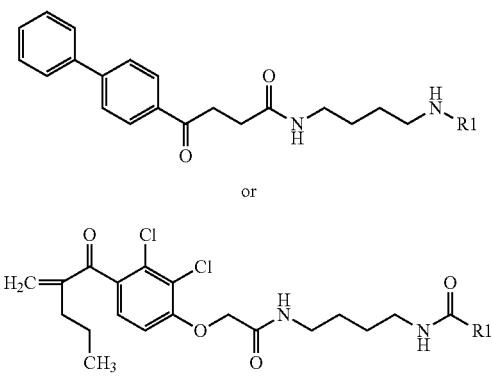

wherein the R1 represents

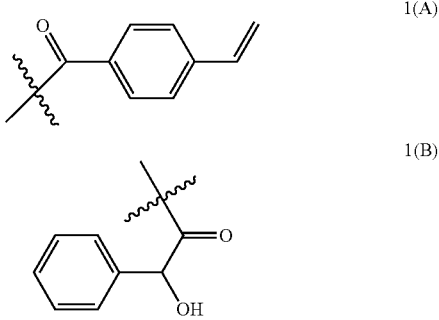

1(C)
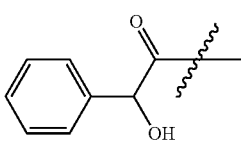
1(D)
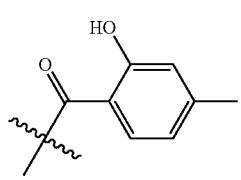
1(E)
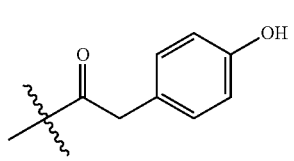
1(F)
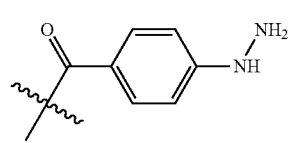
1(G)
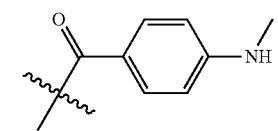
1(H)
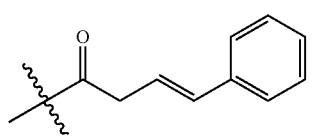
1(I)
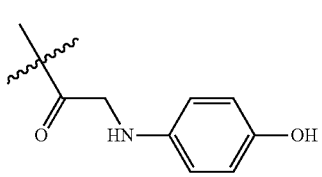
1(J)
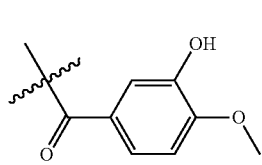
1(K)
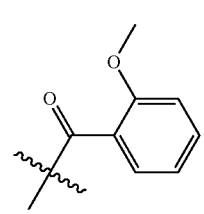
1(L)
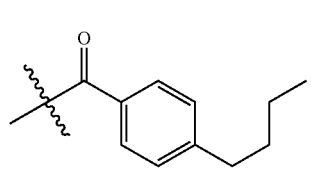
1(M)
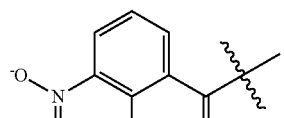
1(N)
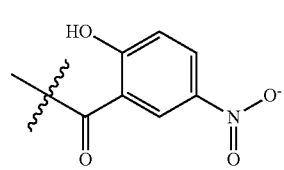
1(O)
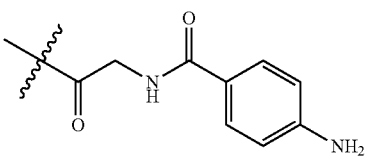
1(P)
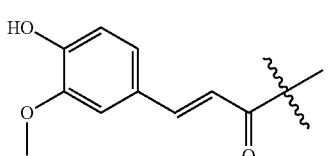
1(Q)
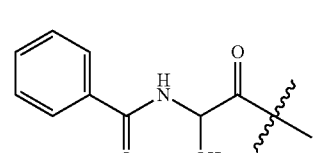
1(R)
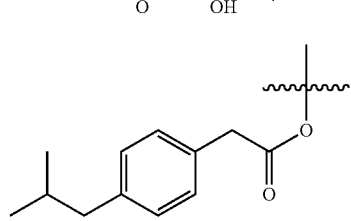
1(S)
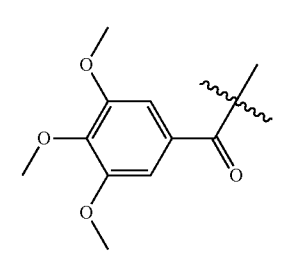
1(T)
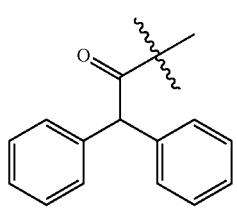
1(U)
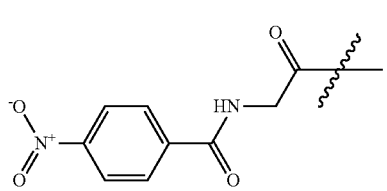

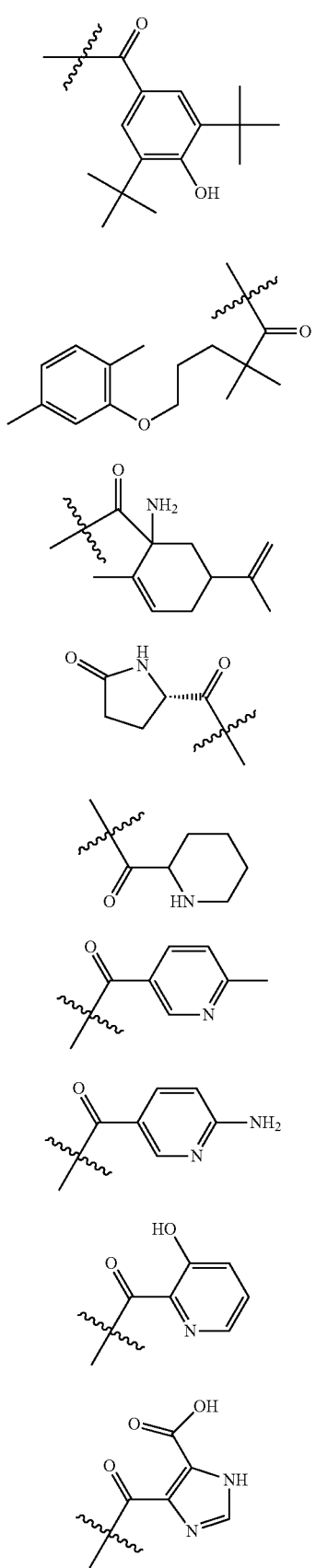
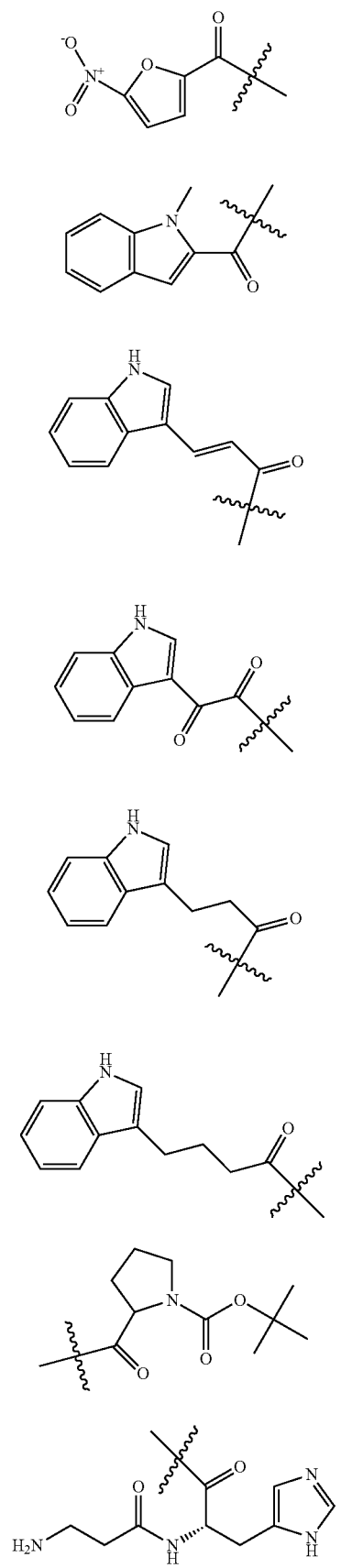

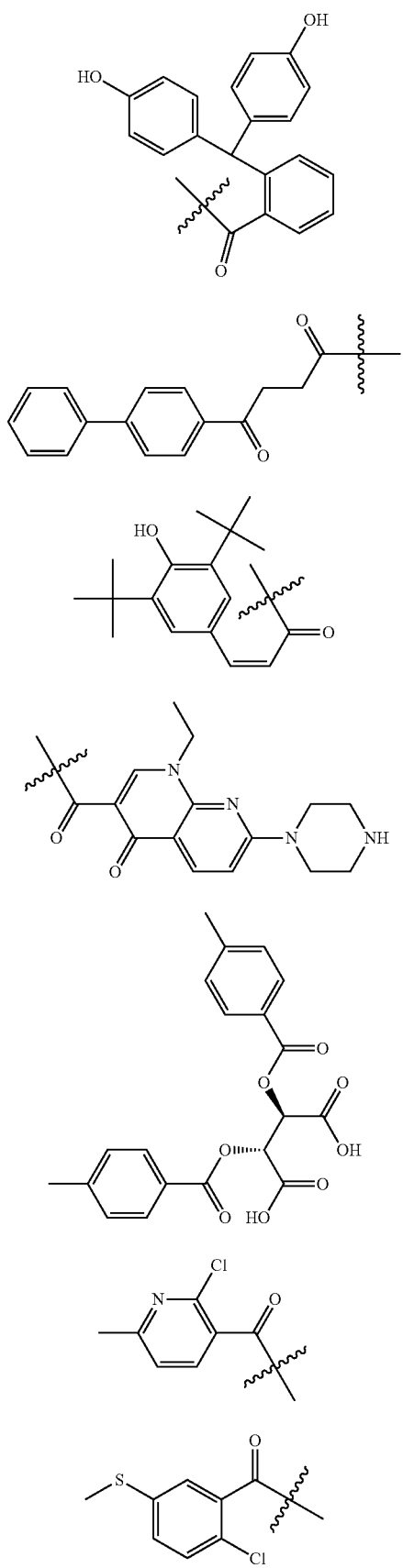
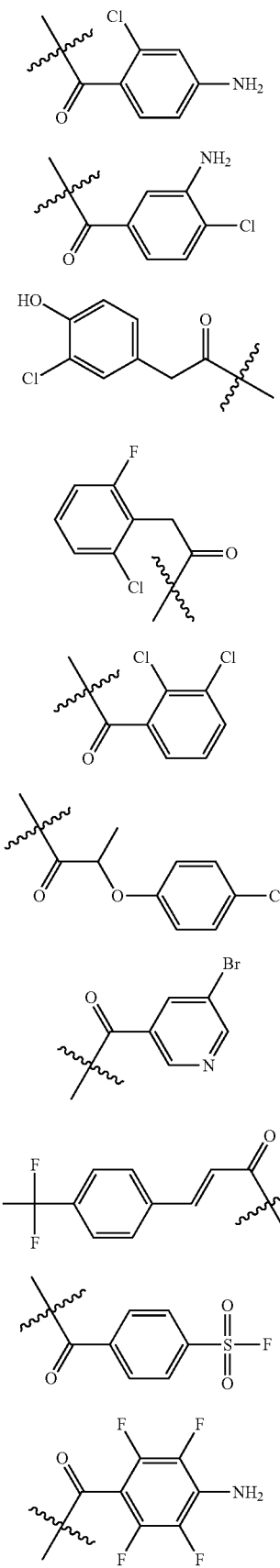

3(M) 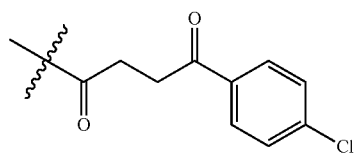
3(N) 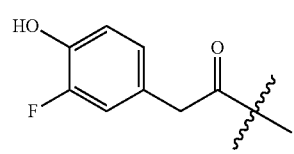
3(O) 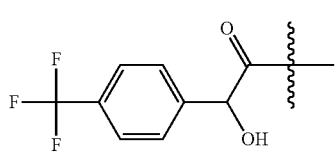
3(P) 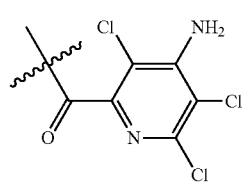
3(Q) 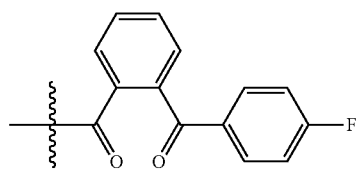
3(R) 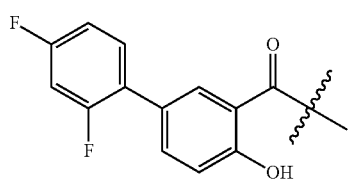
3(S) 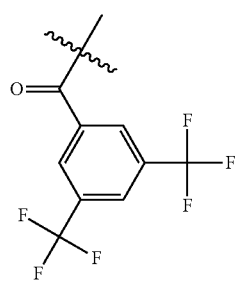
3(T) 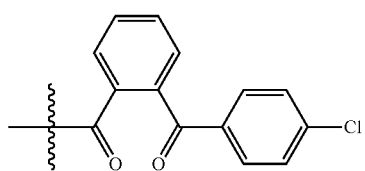
3(U) 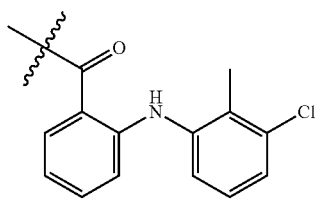
3(V) 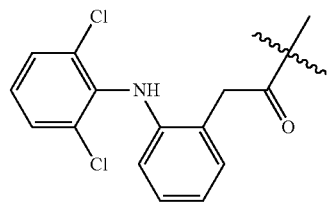
3(W) 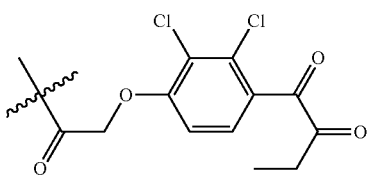
3(X) 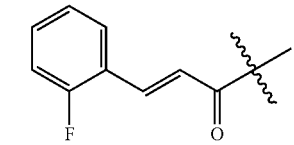
3(Y) 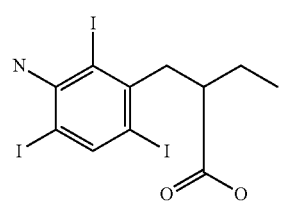
3(Z) 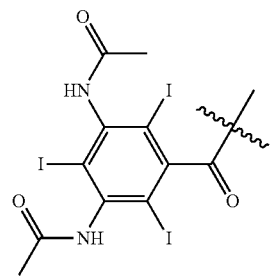
4(A) 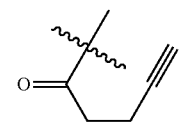
4(B)

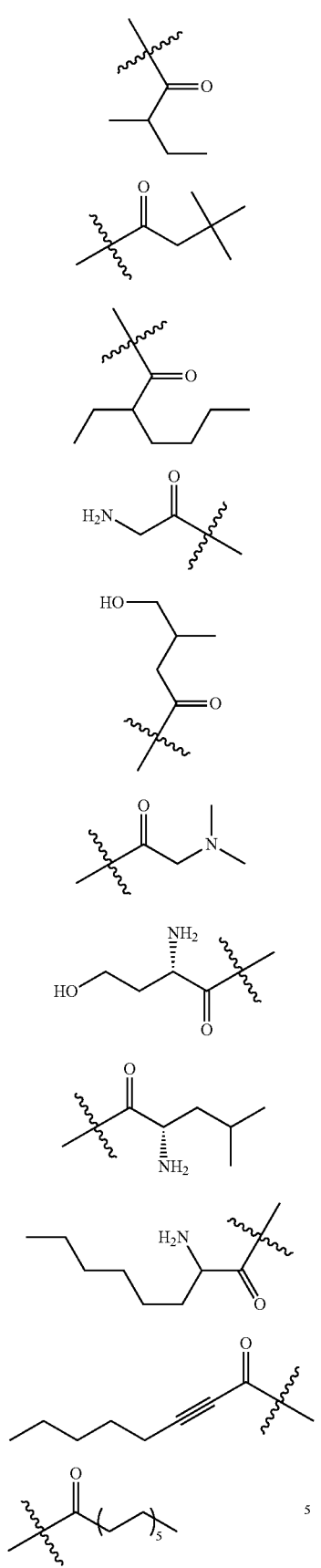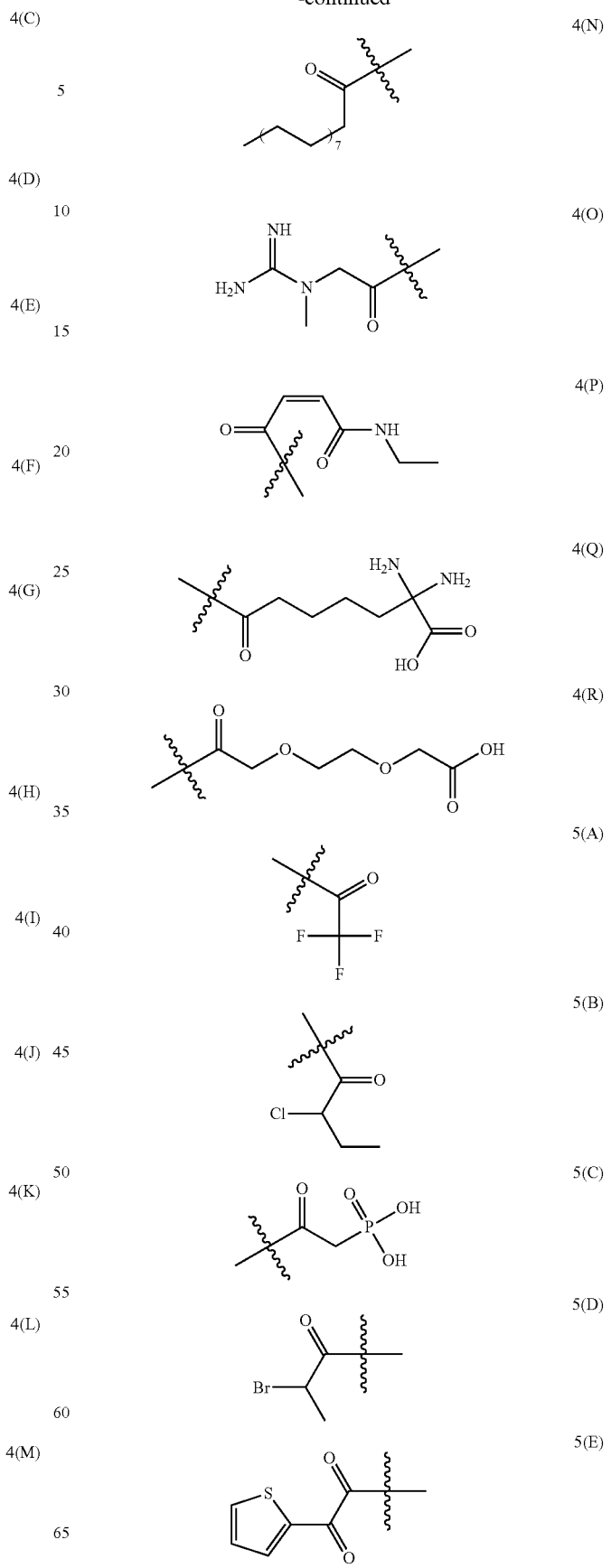

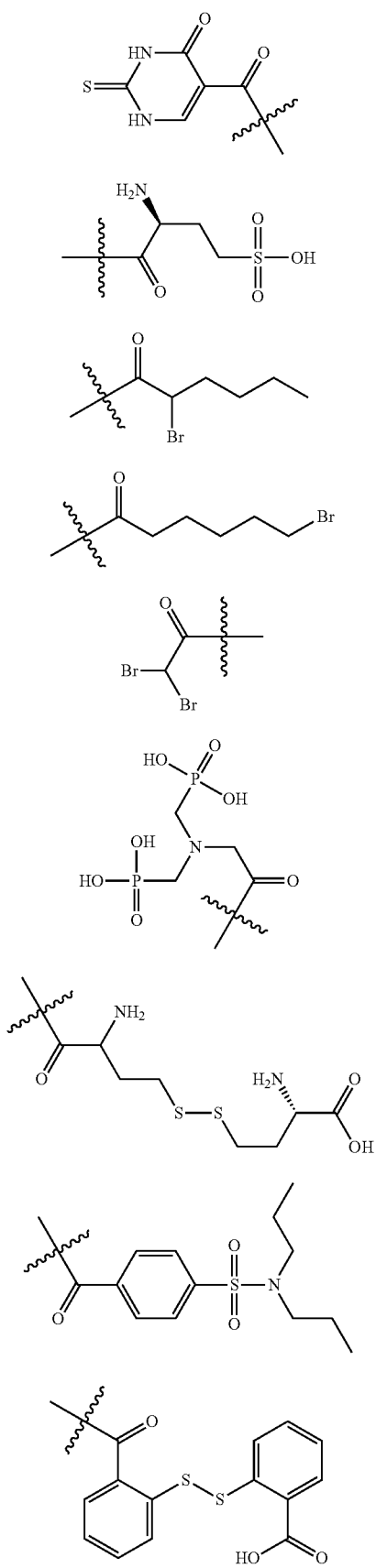

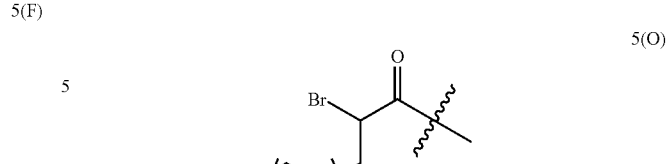

DETAILED DESCRIPTION OF THE INVENTION

Figure 1A:
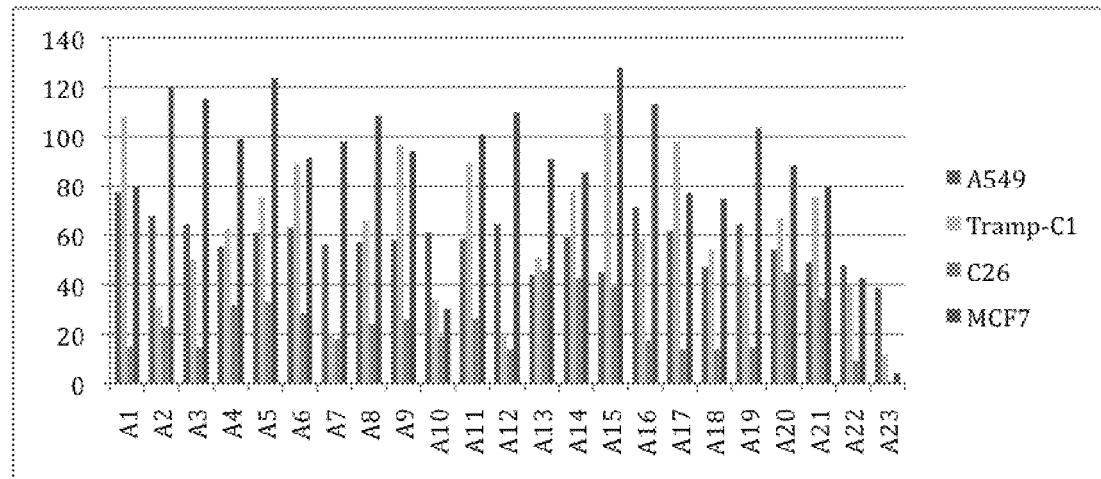
FIG. 1(A) mono-aromatic ring, FIG. 1(B) heteroaromatic, FIG. 1(C) aromatics containing halogen, FIG. 1(D) aliphatics and FIG. 1(E) aliphatic groups containing heteroatoms such as phosphor and aza acids.

In view of the prior art, further deciphering more potent analogs by means of library approach is of interest. Therefore, butyl fenbufen and butyl ethacrynic amide emerged as the building blocks for construction of libraries for further screening assay in the present invention.

Since the structural features of the biphenyl moieties and the aromatic ring moieties are each required for the bioactivities of individual compound class, the optimal structural diversity would be extended from the terminal end on the butyl group. Thus, a bifunctional linker comprising of a protected amino and a free amino group is prerequisite. To this end, various synthetic approaches using either Boc or azido as the protecting groups have been reported (*PLoS ONE*, 12(4) e8294, 2009). Among them, azide as protecting group is used in the present invention due to its easy preparation (*J. Org. Chem.*, 58, 3736-3741, 1993).

A number of synthetic routes toward 4-azido-1-butanamine have been reported e.g. reductive alkylation of an azide (*Tetrahedron Letters*, 42, 2709-2711, 2001) and selective reduction of diazidoalkanes (*Tetrahedron Letters*, 42, 2709-2711, 2001). For shortening the synthesis, here, the present invention describes an alternative route for synthesis of 4-azido-1-butanamine (compound 2) from 4-amino butanamine (compound 1) via azide transfer reaction under the catalysis of copper. The process is performed in solution phase and the reaction temperature is in the range of 0-100° C.

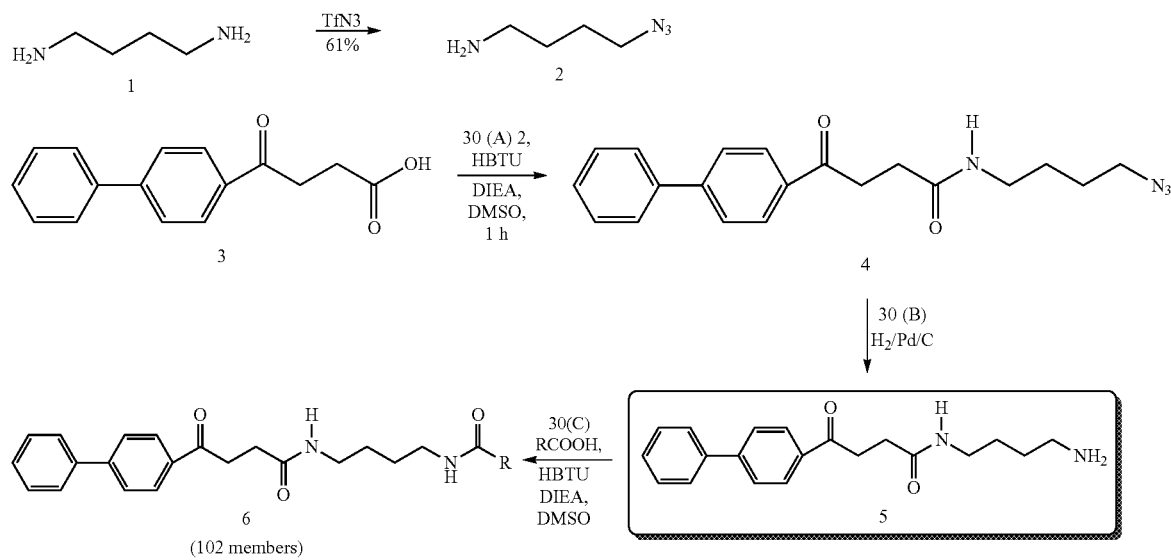

Reagents: 30(A) compound 2, HBTU; 30(B) H2/Pd/C; 30(C)RCOOH.

The advantage of the present method for producing 4-azido-1-butanamine lied in a straightforward purification, thereby simplifying the overall synthesis. Activation of the compound 3 by means of formation of the compound 7 to couple with compound 2 failed; however, to provide satisfactory amount of compound 4 under either room temperature or reflux condition. Thus the usual activation condition using O-(benzotriazol-1-yl)-N,N,N',N'-tetramethyluronium (HBTU) emerged as the proper choice.

Followed by coupling and reductive hydrogenation, the amine compound 5 obtained was readily used for constructing the libraries of compound 6. Likewise, a similar synthetic approach could be used for the preparation of 4-amino butyl ethacrynic amide (compound 10). The two amino compounds 5 and 10 were obtained in 68-70% yields.

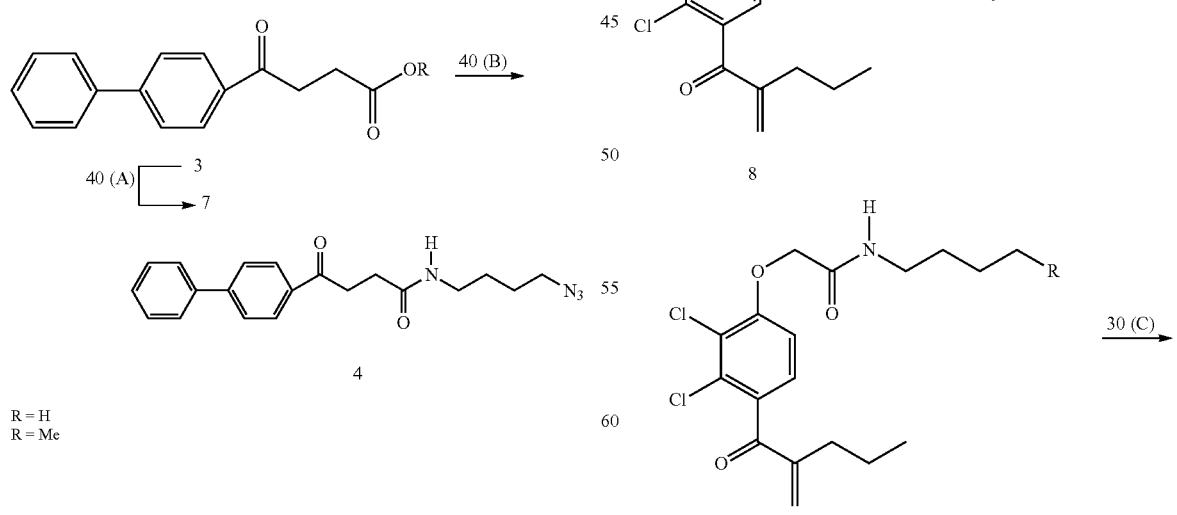

Reagents and condition: 40(A) CH$_2$N$_2$; 40(B)$_2$, NEt$_3$, DMF, rt or reflux, 16%~23%.

-continued

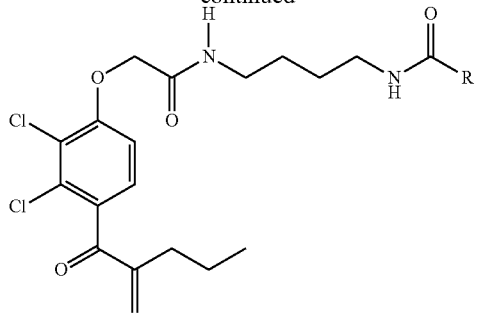

11
(102 members)

R = N₃
R = NH₂

Reagents: 30(A) compound 2, HBTU; 30(B) H2/Pd/C; 30(C)RCOOH.

In order to high throughput construct and screen potential compound for treating cancer. The solution-phase combinatorial chemistry is used in the present invention to produce the libraries of fenbufen and ethacrynic acid. The present invention provides a compound of formula:

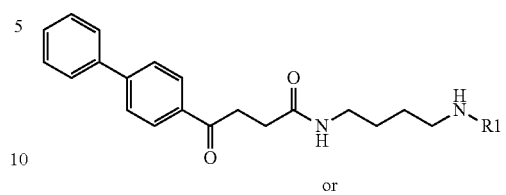

or

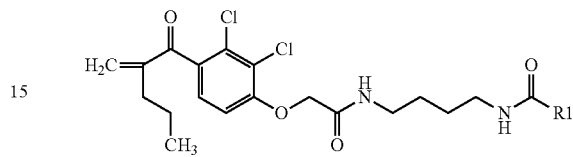

wherein the R1 is represents acetyl.

In the embodiment of the invention, R1 contains aromatic ring, heterocyclic ring, halo aromatic ring, aliphatic chain or heteroaliphatic chain. In the more embodiment of the invention, the compound is N-(4-(4-(biphenyl-4-yl)-4-oxobutanamido)butyl)-5-(2,5-dimethylphenoxy)-2,2-dimethylpentanamide,

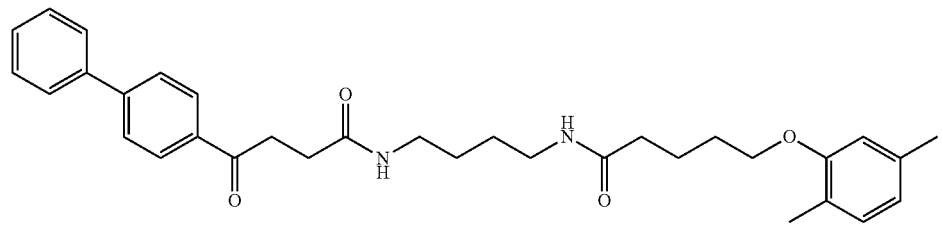

N-(4-(4-(biphenyl-4-yl)-4-oxobutanamido)butyl)-2-ethylhexanamide

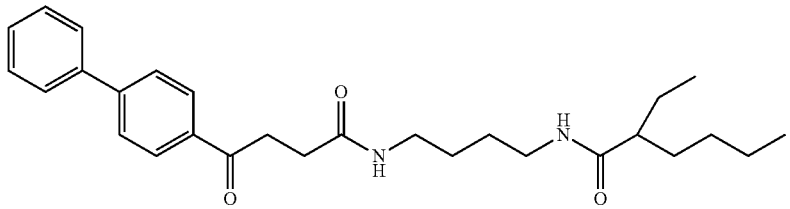

or 4-(biphenyl-4-yl)-N-(4-(2-(2,3-dichloro-4-(2-methylenebutanoyl)phenoxy)acetamido)butyl)-4-oxobutanamide

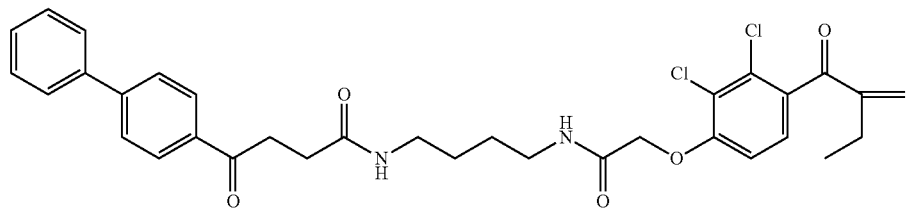

The present invention provides a combinatorial library of cytotoxicity compounds comprising a plurality of compound of formula:
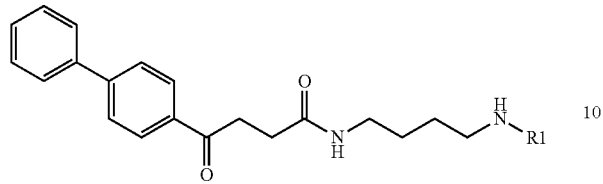
or
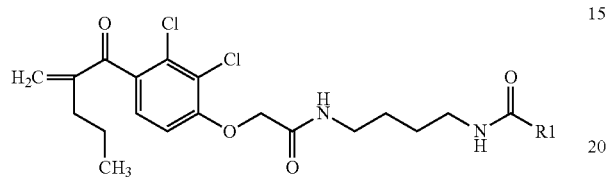
wherein the R1 represents
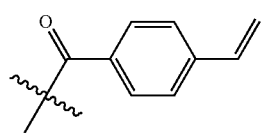
1(A)
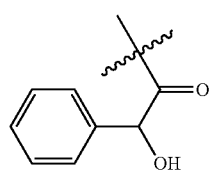
1(B)
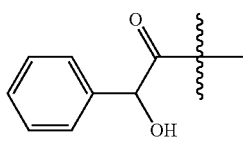
1(C)
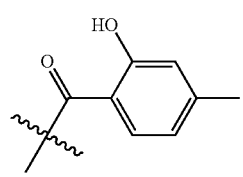
1(D)
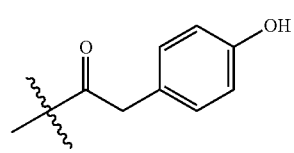
1(E)
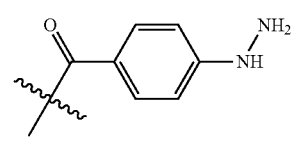
1(F)
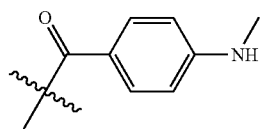
1(G)
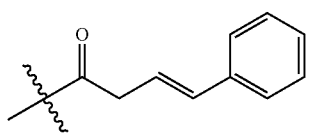
1(H)
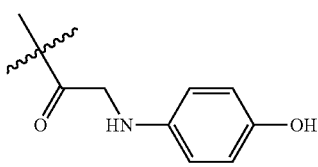
1(I)
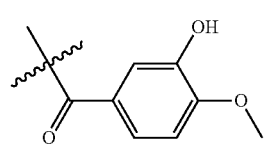
1(J)
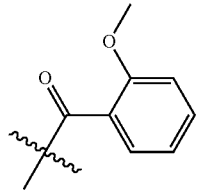
1(K)
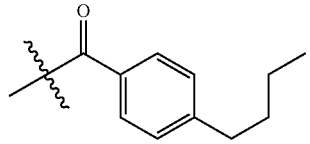
1(L)
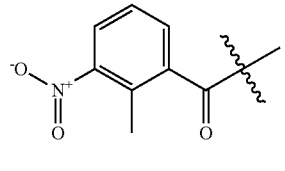
1(M)
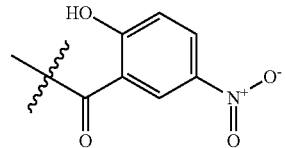
1(N)
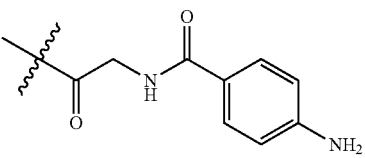
1(O)
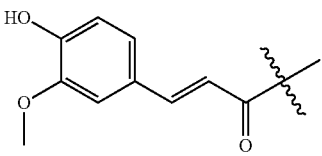
1(P)

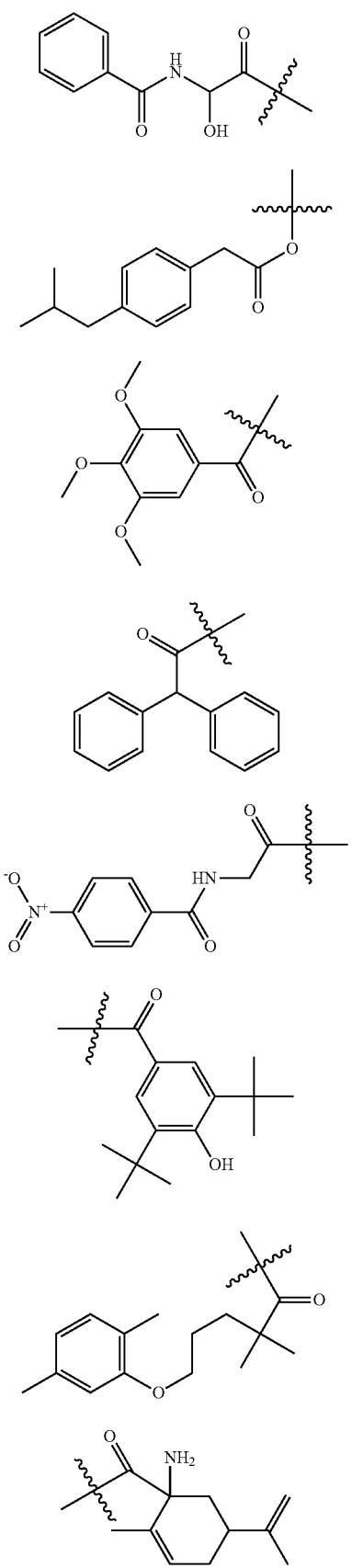
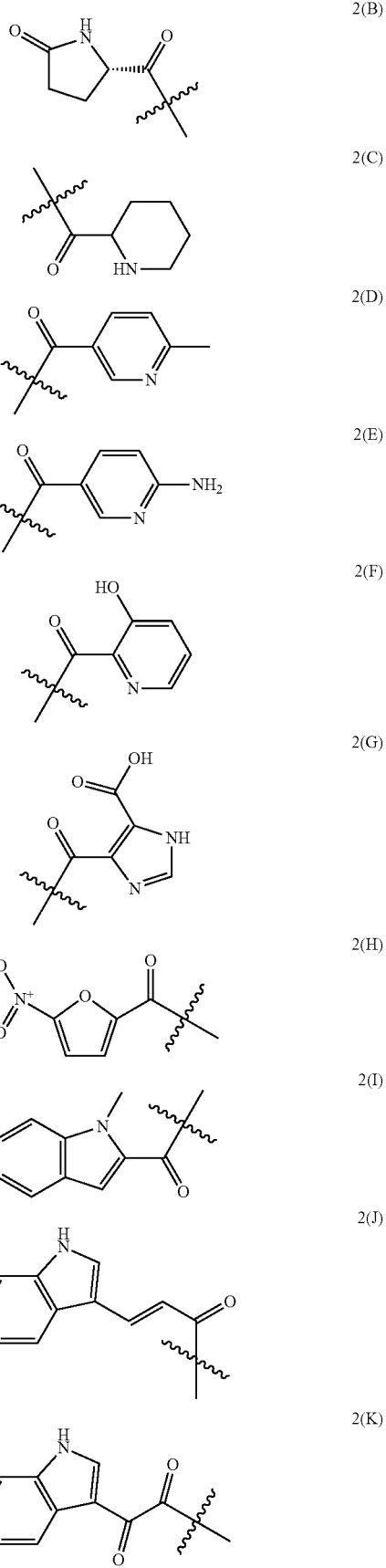

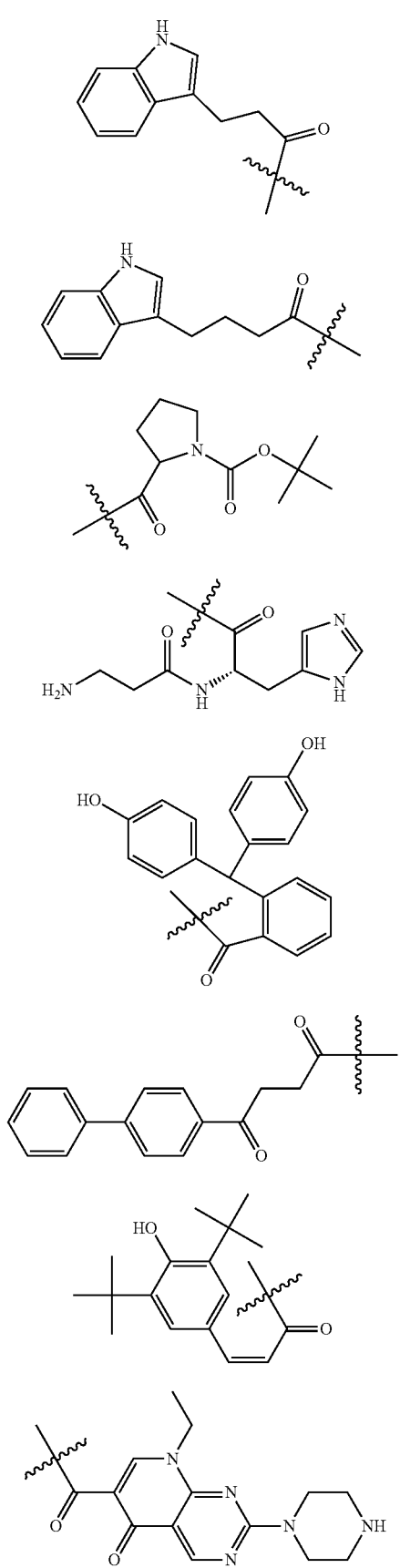
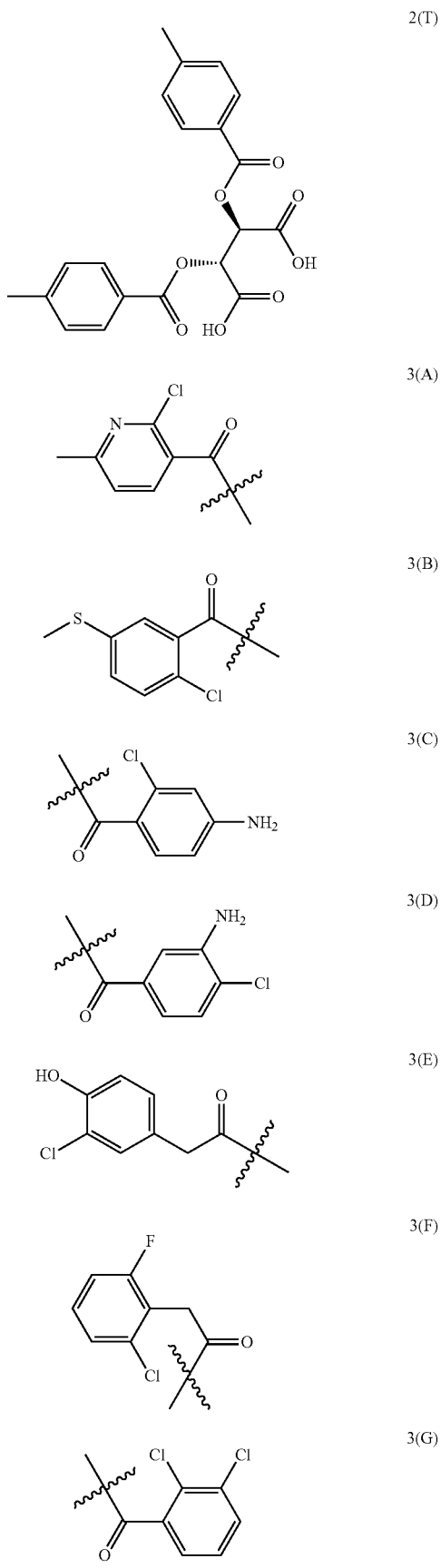

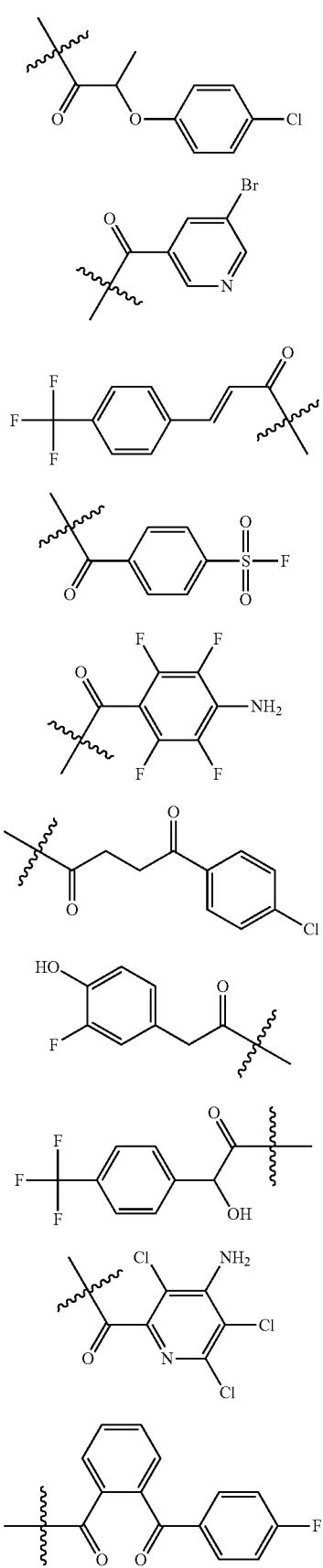
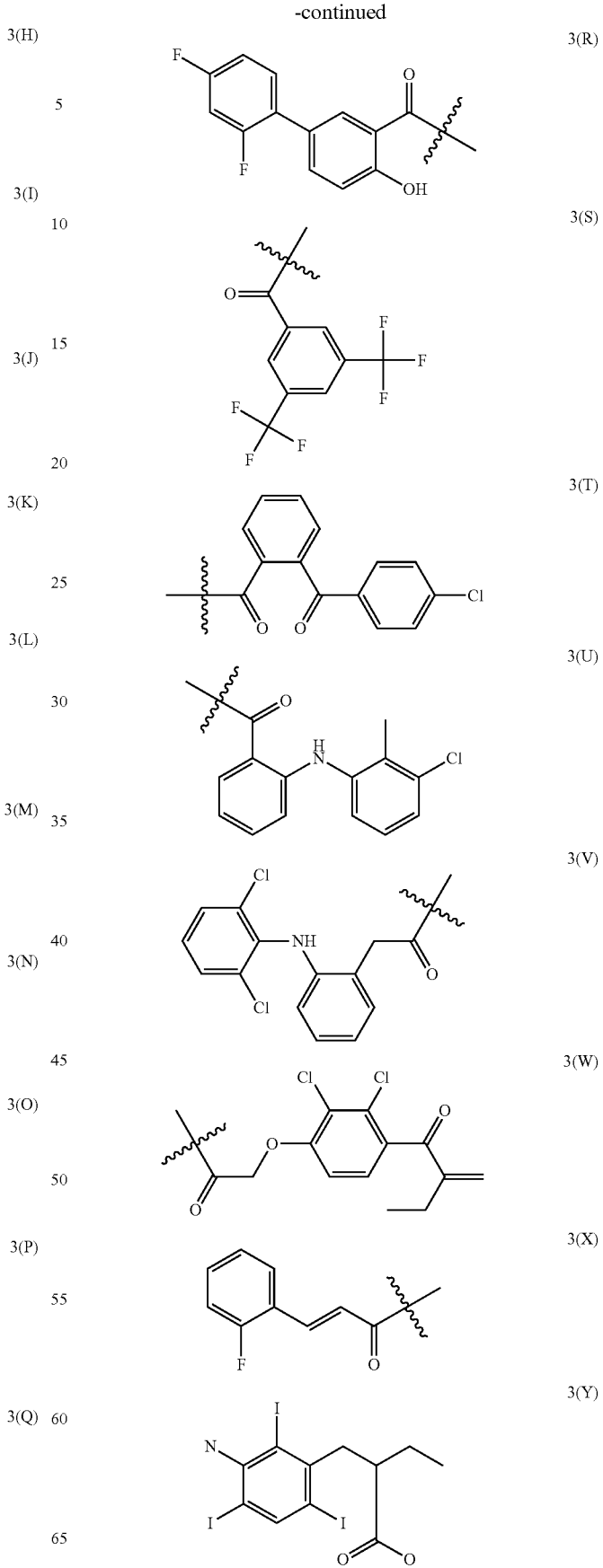

3(Z)
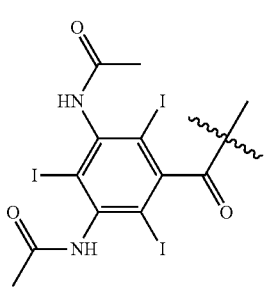
4(A)
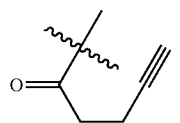
4(B)
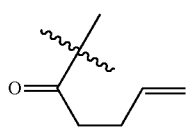
4(C)
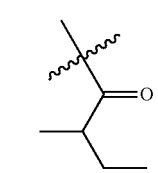
4(D)
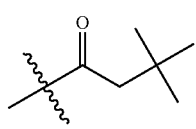
4(E)
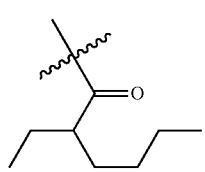
4(F)
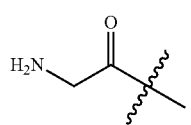
4(G)
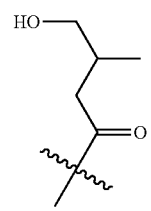
4(H)
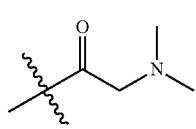
4(I)
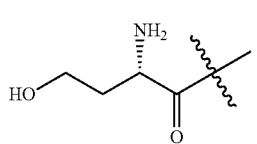
4(J)
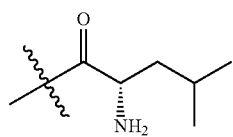
4(K)
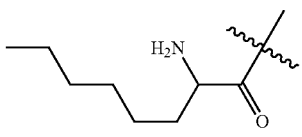
4(L)
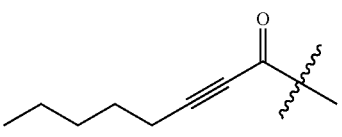
4(M)
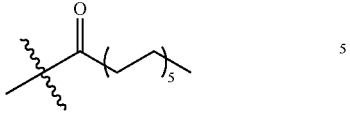
4(N)
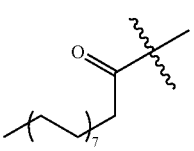
4(O)
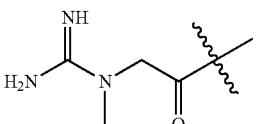
4(P)
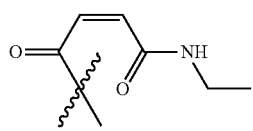
4(Q)
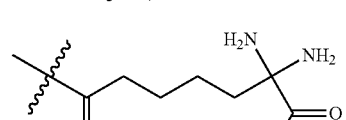
4(R)
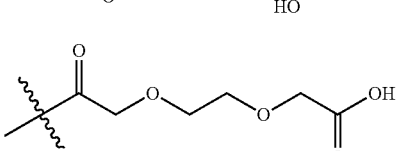
5(A)
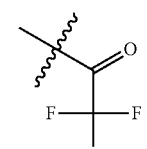
5(B)
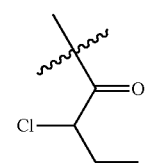

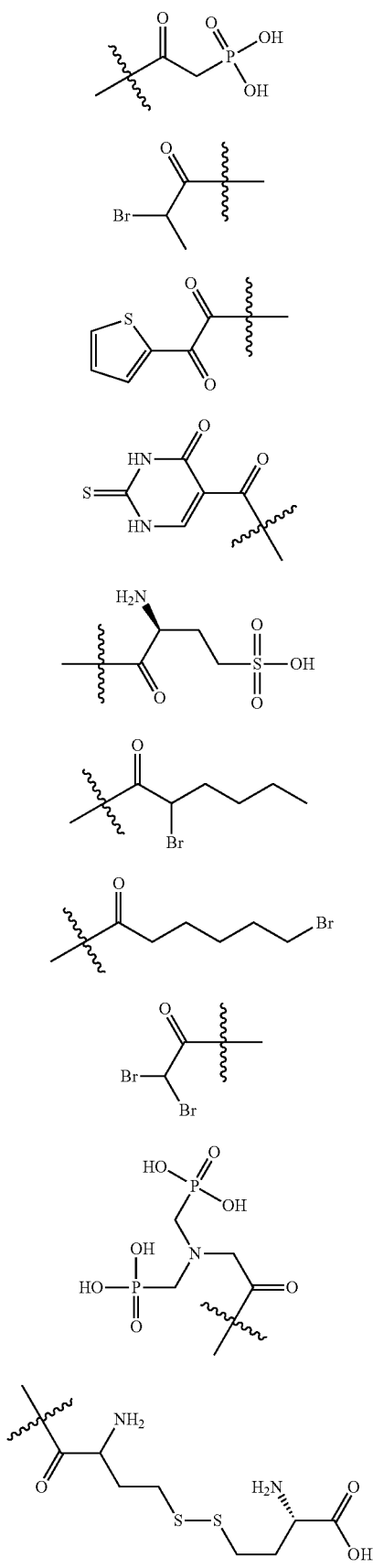
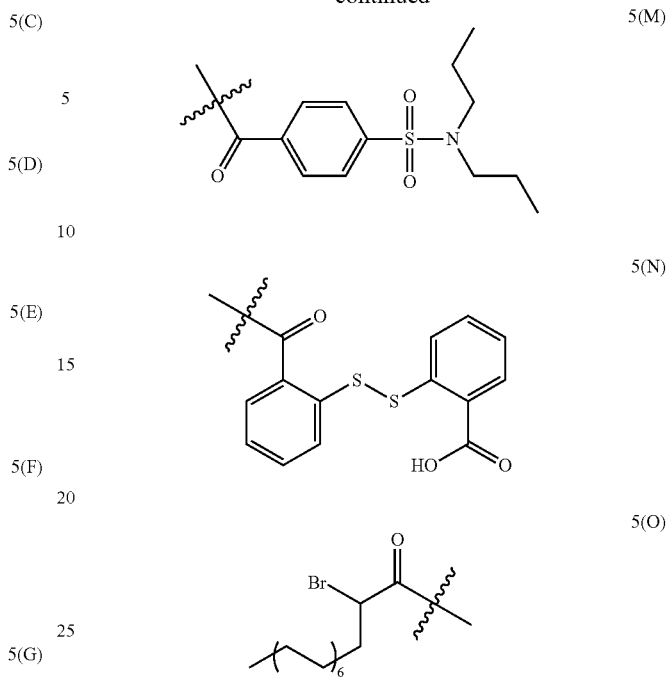

The present invention also provides a method for inducing cytotoxicity in a subject comprising administering the subject the compound having the structure:

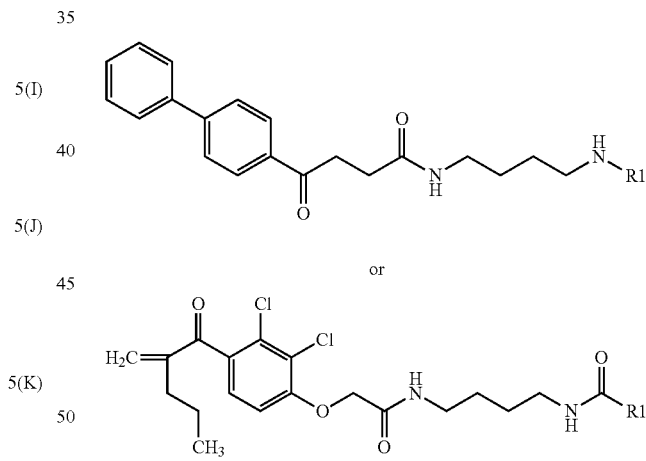

wherein the R1 represents acetyl.

The subject used herein is a cell, a tissue or a mammal. In the embodiment of the invention, the subject is a mammal. In more embodiment of the invention, the mammal is human. The compound used for inducing cytotoxicity is N-(4-(4-(biphenyl-4-yl)-4-oxobutanamido)butyl)-5-(2,5-dimethylphenoxy)-2,2-dimethylpentanamide, N-(4-(4-(biphenyl-4-yl)-4-oxobutanamido)butyl)-2-ethylhexanamide or 4-(biphenyl-4-yl)-N-(4-(2-(2,3-dichloro-4-(2-methylenebutanoyl)phenoxy)acetamido)butyl)-4-oxobutanamide.

Moreover, the present invention provides a method for inhibiting the proliferation of tumor cells comprising administering to said tumor cells an inhibitory amount of the compound of formula:

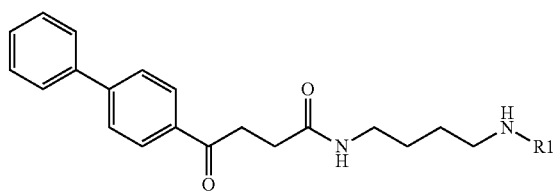

or

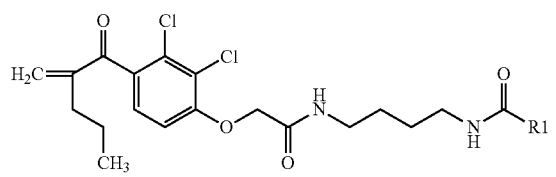

wherein the R1 represents acetyl.

In the embodiment of the invention, the compound is N-(4-(4-(biphenyl-4-yl)-4-oxobutanamido)butyl)-5-(2,5-dimethylphenoxy)-2,2-dimethylpentanamide, N-(4-(4-(biphenyl-4-yl)-4-oxobutanamido)butyl)-2-ethylhexanamide or 4-(biphenyl-4-yl)-N-(4-(2-(2,3-dichloro-4-(2-methylenebutanoyl)phenoxy)acetamido)butyl)-4-oxobutanamide. The compound inhibits C26, A549, MCF-7 and TRAMP-C1 cell line proliferation. Therefore the tumor cell mentioned here includes but not limited to colon carcinoma, epithelial carcinoma, breast carcinoma or prostate cancer cell.

EXAMPLE

Example 1

Compounds Synthesis

General Procedure for Coupling of the Amino Compounds with Carboxylic Acids in Solution Phase The reagents used in the amide bond formation were core amine (1 mg, 4 μmol), carboxylic acid (1 eq), n,n-Diisopropylethyamine (DIEA, 1.2 eq) and 2-(1H-Benzotriazole-1-yl)-1,1,3,3-tetramethyluronium hexafluorophosphate (HBTU, 1.1 eq). Both the starting core amine and the carboxylic acids were prepared as a stock solution of DMSO at a concentration of 0.1 mmol/200 mL and 5 mmol/10 mL, respectively. HBTU and DIEA were dissolved in DMSO as a concentration of 5 mmol/10 mL, respectively. Each of the acid portion was firstly mixed with HBTU in an plastic tube for 30 sec, followed by the addition of a mixture of core amine (10 mL) and DIEA (10 mL) in a total volume of 40 mL. All vials were shook for 1 min. A portion of the mixture (10 mL) was transferred to a novel tube followed by addition of 990 mL of water.

In this present invention, carboxylic acid moieties were structurally classified in five types as follows: mono-aromatic ring (Table 1-1), heteroaromatic (Table 1-2), aromatics containing halogen (Table 1-3), aliphatics (Table 1-4) and aliphatic groups containing heteroatoms such as phosphor and aza acids (Table 1-5).

TABLE 1-1

Acid moieties containing aromatic ring

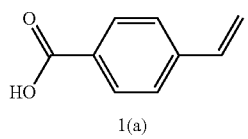
1(a)

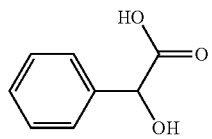
1(b)

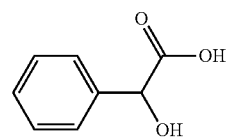
1(c)

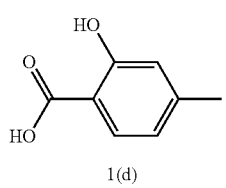
1(d)

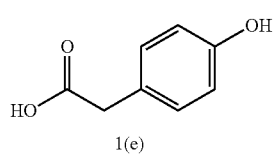
1(e)

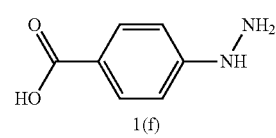
1(f)

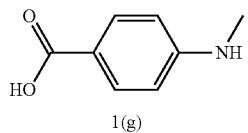
1(g)

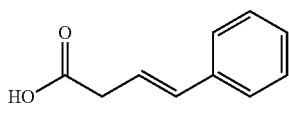
1(h)

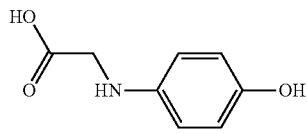
1(i)

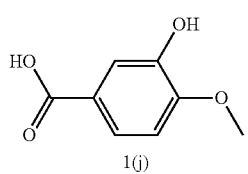
1(j)

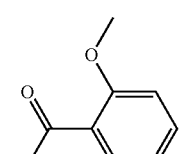
1(k)

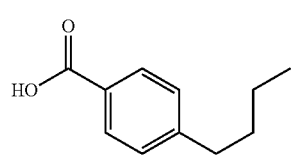
1(l)

TABLE 1-1-continued

Acid moieties containing aromatic ring

1(m) 1(n) 1(o)

1(p) 1(q) 1(r)

1(s) 1(t) 1(u)

1(v) 1(w)

TABLE 1-2

Acid moieties containing heterocyclic ring

2(a) 2(b) 2(c)

2(d) 2(e) 2(f)

TABLE 1-2-continued
Acid moieties containing heterocyclic ring
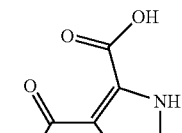
2(g)
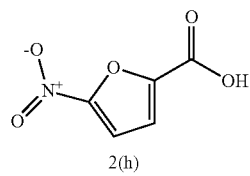
2(h)
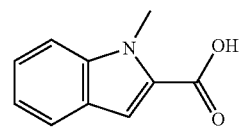
2(i)
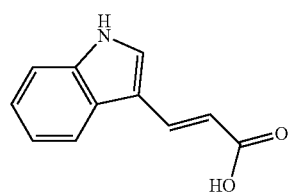
2(j)
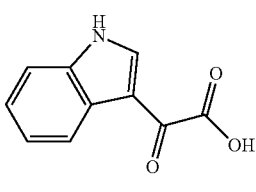
2(k)
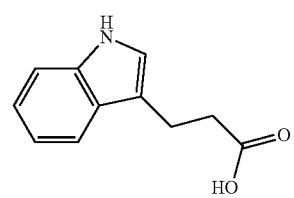
2(l)
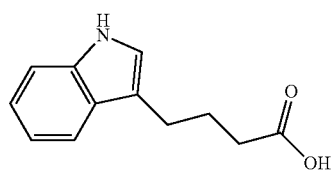
2(m)
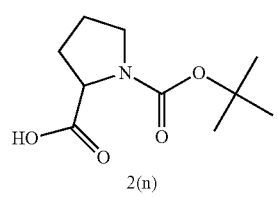
2(n)
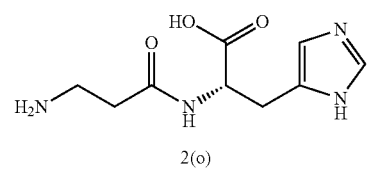
2(o)
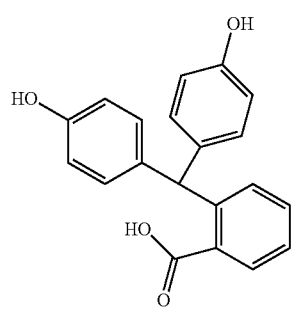
2(p)
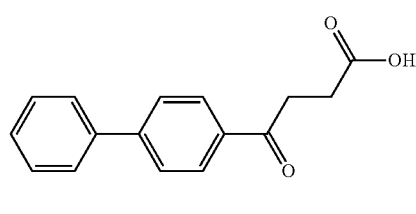
2(q)
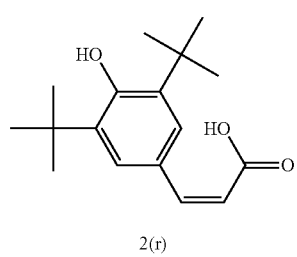
2(r)
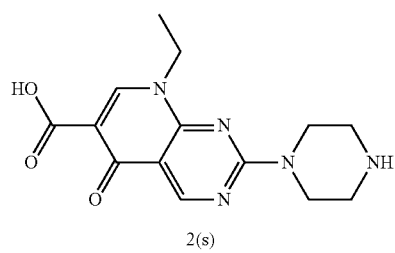
2(s)
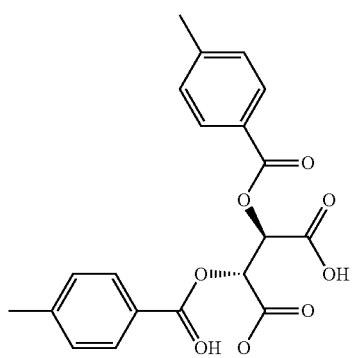
2(t)

TABLE 1-3
Acid moieties containing halo aromatic ring
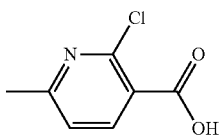
3(a)
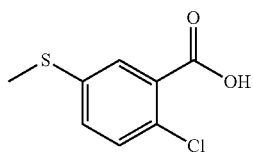
3(b)
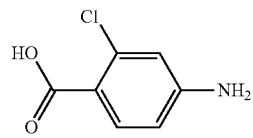
3(c)
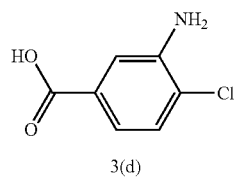
3(d)
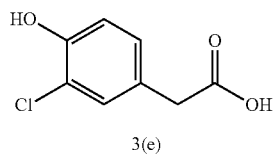
3(e)
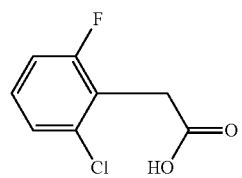
3(f)
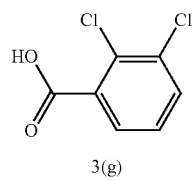
3(g)
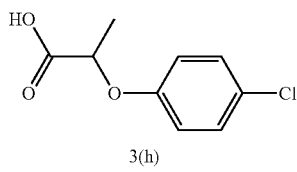
3(h)
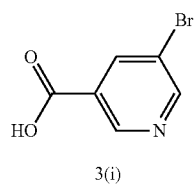
3(i)
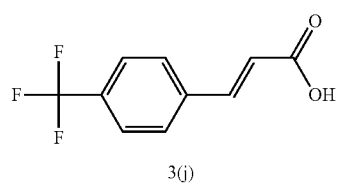
3(j)
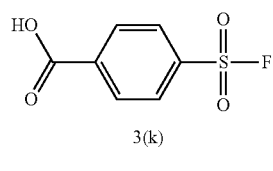
3(k)
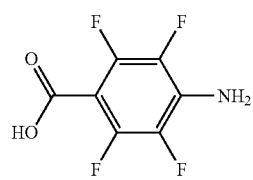
3(l)
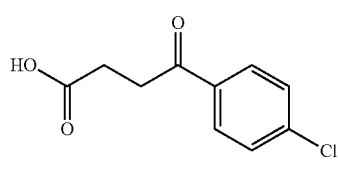
3(m)
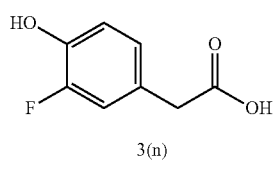
3(n)
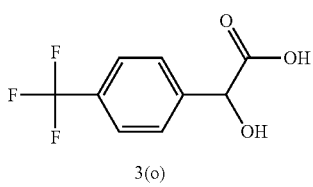
3(o)
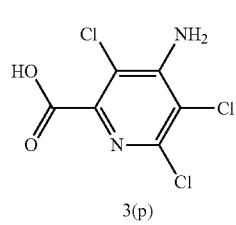
3(p)
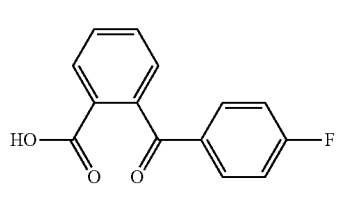
3(q)
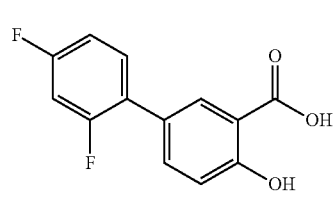
3(r)
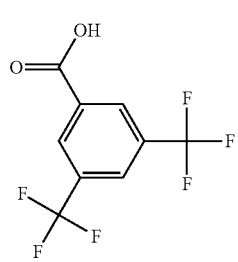
3(s)
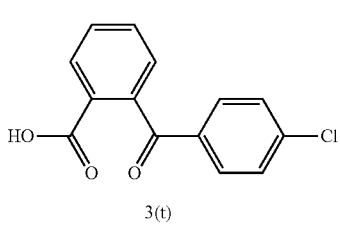
3(t)
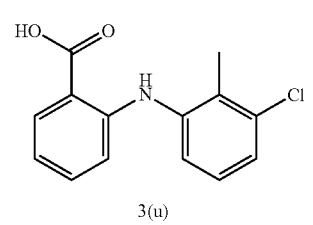
3(u)

TABLE 1-3-continued
Acid moieties containing halo aromatic ring
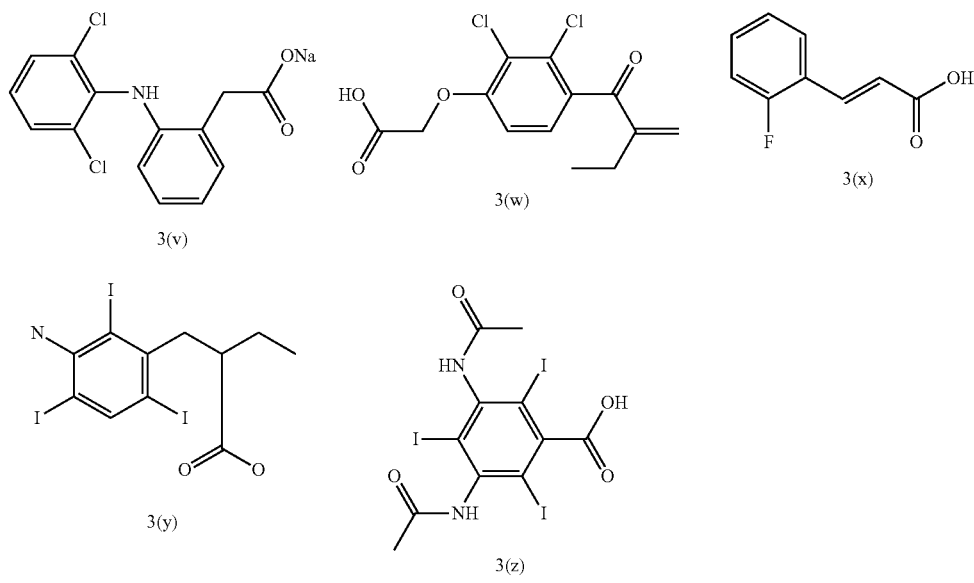
TABLE 1-4
Acid moieties containing aliphatic chain
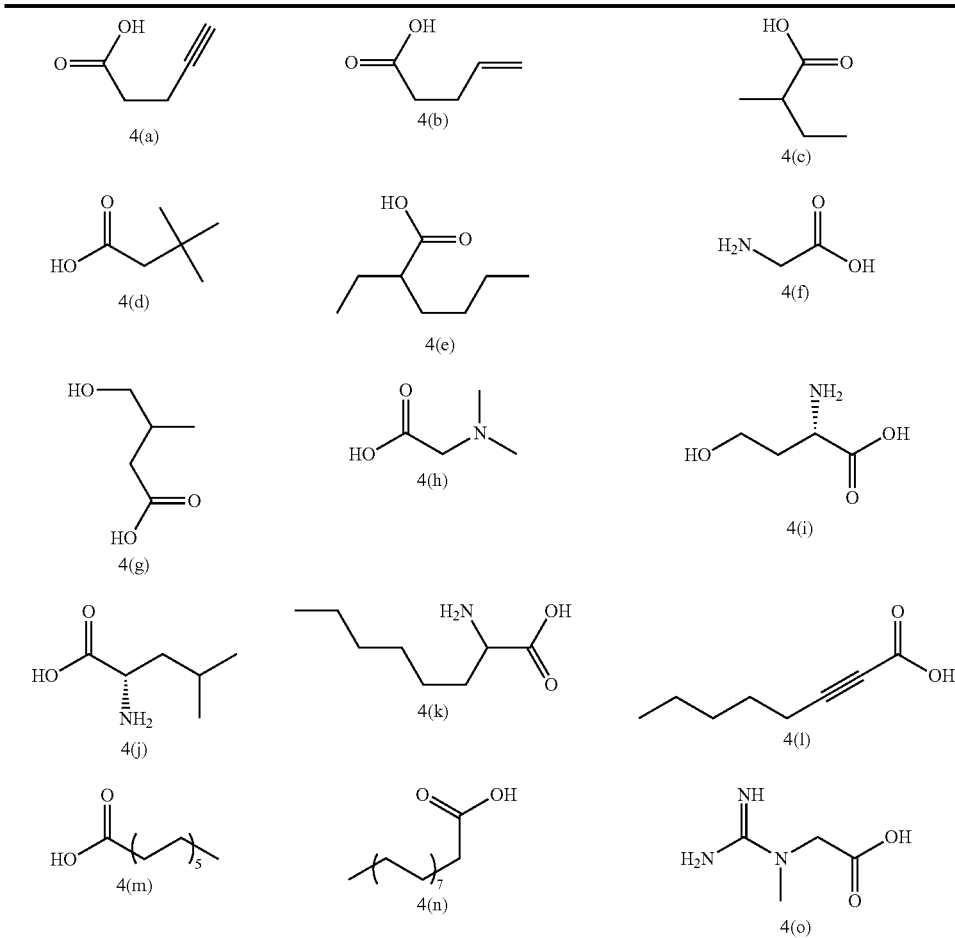

TABLE 1-4-continued

Acid moieties containing aliphatic chain

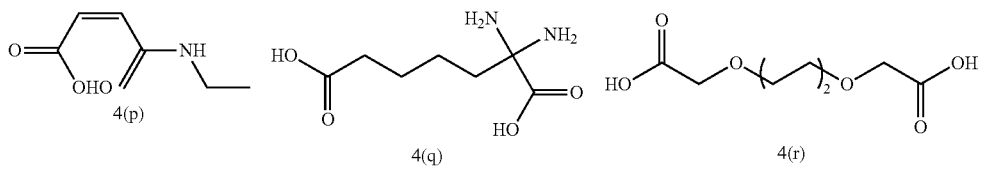

TABLE 1-5

Acid moieties containing heteroaliphatic chain

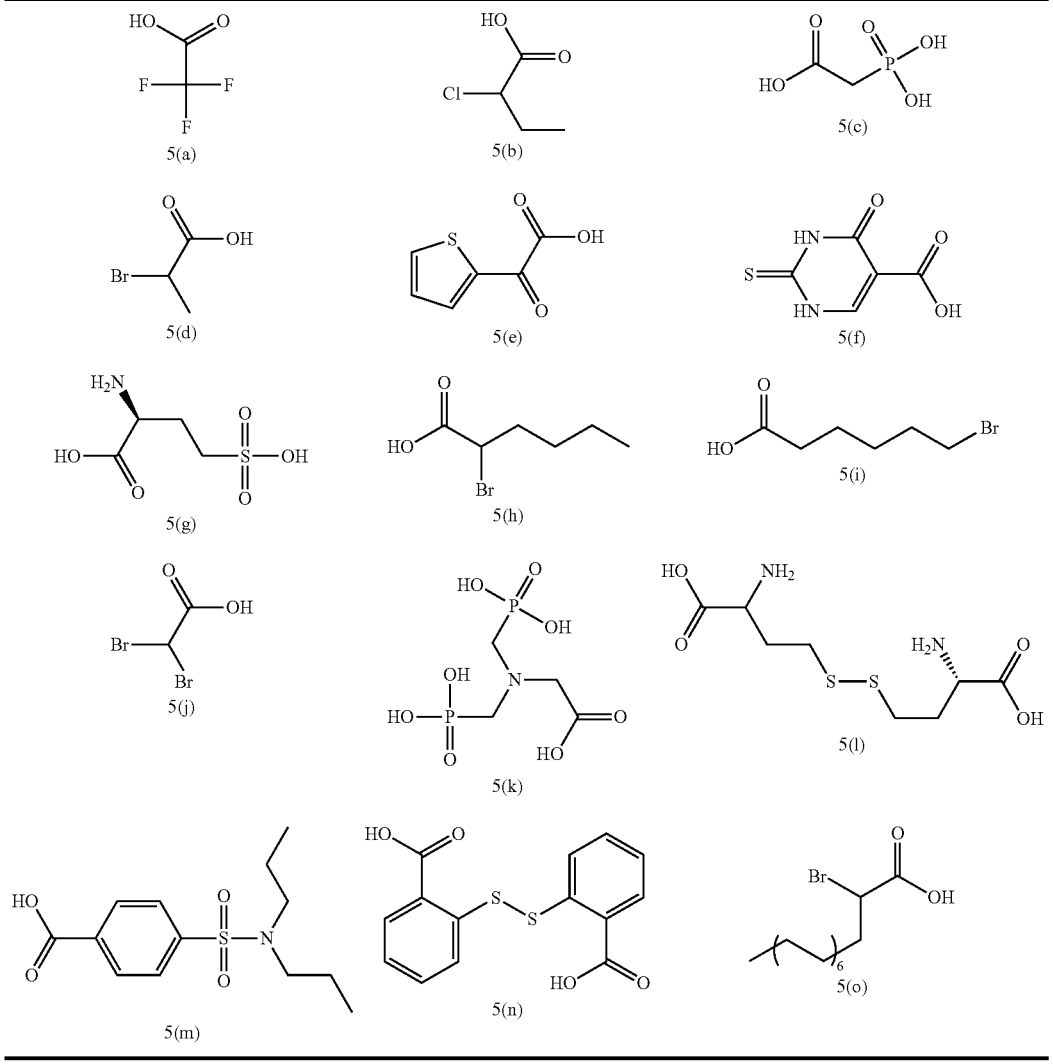

4-azido-1-butanamine (compound 2)

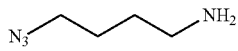

1) Preparation of TfN$_3$: NaN$_3$ (9.7 g, 150 mmol) was dissolved in H$_2$O (10 mL) at 2° C. A solution of Tf$_2$O (5 mL, 30 mmol) dissolved in CH$_2$Cl$_2$ (15 mL) was added. The biphasic mixture was stirred vigorously for 1 hr. Following the colleting organic layer, the water phase was extracted using CH$_2$Cl$_2$ (5 mL). The organic phase were combined and washed with NaHCO$_3$ (10 mL) twice to provide TfN$_3$. 2) Azide transfer reaction: To a solution of butane-1,4-diamine (1 mL, 880 mg, 10 mmol) dissolving in H$_2$O (25 mL) was added K$_2$CO$_3$ (2 g, 15 mmol), CuSO$_4$ (16 mg, 0.1 mmol) and the above solution of TfN$_3$, sequentially. The mixture was brought about to a homogeneous solution by addition of MeOH (100 mL). TLC (MeOH: CHCl$_3$: NH$_{3(aq)}$=1:1:0.02) indicated the consumption of starting material (R$_f$=0.05) and the formation of the product 2 (R$_f$=0.48). After 18 hr, the mixture was submitted to partition by addition of NaOH (1 N, 20 mL) and CH$_2$Cl$_2$ (60 mL). The organic layer collected was extracted by another portion of NaHCO$_3$ (25 mL). Butane-1,4-amine and organic salts could be removed during this procedure. After concentration under reduced pressure at 30° C., a pale yellow oil was obtained in 61% yield (695 mg).

Anal. C$_4$H$_{10}$N$_4$, MW=114.2, ESI+Q-TOF: M=114.1 (m/z), [M+H]$^+$=115.1, [M+Na]$^+$=137.1, [2M+Na]$^+$=251.2; $^1$H-NMR (500 MHz, CDCl$_3$): δ 1.55-1.67 (m, 4H, aliphatic-H), 1.8 (s, 2H, Amine-H), 3.20-3.34 (m, 4H, aliphatic-H); $^{13}$C-NMR (125 MHz, CDCl$_3$): δ 18.27 (CH$_2$), 28.42 (CH$_2$), 30.51 (CH$_2$), 49.60 (CH$_2$).

4-azidobutan-1-ol (compound 3)

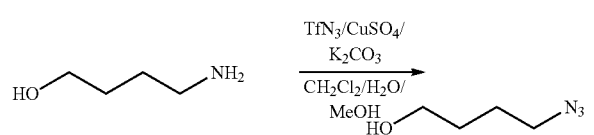

The preparation followed the same procedure for 4-azido-1-butanamine as described above. NaN$_3$ (9.7 g, 150 mmol), H$_2$O (7 mL), a solution of Tf$_2$O in CH$_2$Cl$_2$ (14 mL) were used. Extraction was performed by using NaHCO$_3$ (27 mL) and CH$_2$C$_2$ (63 mL). The following azide transfer reaction followed the same procedure as above. A pale yellow gel-like product was obtained in 70% yield (800 mg).

Anal. C$_4$H$_9$N$_3$O, MW=114.2, ESI+Q-TOF: M=115.1 (m/z), [M+H]$^+$=116.1; $^1$H-NMR (500 MHz, CDCl$_3$): δ 1.55-1.67 (m, 4H, aliphatic-H), 3.25 (dd, 2H, J=6.5 Hz, aliphatic-H), 3.59 (dd, 2H, J=6.0 Hz, aliphatic-H); $^{13}$C-NMR (125 MHz, CDCl$_3$): δ 24.92 (CH$_2$), 29.20 (CH$_2$), 50.83 (CH$_2$), 61.24 (CH$_2$).

N-(4-azidobutyl)-4-(biphenyl-4-yl)-4-oxobutanamide (compound 4)

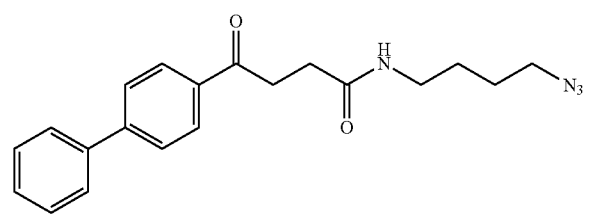

A solution of fenbufen (214 mg, 0.8 mmol), HBTU (302 mg, 0.8 mmol), DIEA (1 mL, 0.8 mmol) and DMF (15 mL) was stirred. 4-azido-1-butanamine was added. TLC (acetone/n-hexane=3/7) indicated the consumption of starting material (R$_f$=0.39) and the formation of the product (R$_f$=0.78). After stirring for 1 hr, the mixture was concentrated under high vacuum at 60° C. The residue was purified by flash chromatography using acetone: n-hexane=3:7 as eluents to provide a snow-white solid in 77% yield (269 mg).

Anal. C$_{20}$H$_{22}$N$_4$O$_2$, MW=350.4, ESI+Q-TOF: M=350.2 (m/z), [M+H]$^+$=351.2 [2M+H]$^+$=701.3; $^1$H-NMR (500 MHz, CDCl$_3$): δ 1.54-1.66 (m, 4H, butyl-H), 2.63 (t, J=6.5 Hz, 2H, aliphatic-H), 3.28 (dd, 4H, aliphatic-H), 3.39 (t, J=6.0 Hz, 2H, aliphatic-H), 5.96 (s, H, NH), 7.35-7.42 (m, 1H, Ar—H), 7.42-7.49 (m, 2H, Ar—H), 7.58-7.62 (m, 2H, Ar—H); 7.67 (d, J=9.0 Hz, 2H, Ar—H), 8.04 (d, J=9.0 Hz, 2H, Ar—H); $^{13}$C-NMR (125 MHz, CDCl$_3$): δ 26.17 (CH$_2$), 26.81 (CH$_2$), 26.85 (CH$_2$), 30.21 (CH$_2$), 30.28 (CH$_2$), 34.18 (CH$_2$), 39.02 (CH$_2$), 39.11 (CH$_2$), 51.01 (CH$_2$), 127.05 (Ar, CH), 127.24 (Ar, CH), 128.26 (Ar, CH), 128.67 (Ar, CH), 128.94 (Ar, CH), 135.07 (Ar, C), 139.75 (Ar, C), 146.04 (Ar, C), 172.38 (HNC=O), * 172.57 (HNC=O), * 198.80 (Ar—C=O—CH$_2$). *: hydrogen bond couplings N-(4-aminobutyl)-4-(biphenyl-4-yl)-4-oxobutanamide (compound 5)

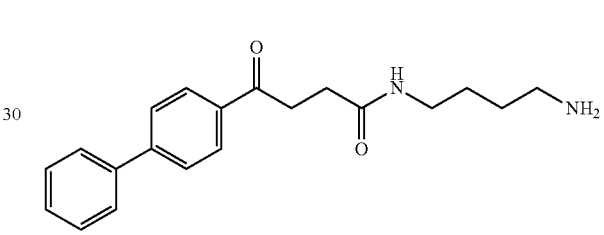

A mixture of compound 3 (240 mg, 0.68 mmol), Pd/C (24 mg) and MeOH (12 mL) was stirred. The mixture sealed with septum was evacuated through syringe and filled by a balloon of H$_2$. After repeating the procedure twice, the mixture was vigorously stirred under a H2 atmosphere for 50 min. TLC (MeOH:CHCl$_3$:NH$_{3(aq)}$=1:1:0.02) indicated the consumption of starting material (R$_f$=0.94) and the formation of the product (R$_f$=0.51). The mixture was filtered and the filtrate was concentrated under reduced pressure at 80° C. The residue was partitioned by adding an aqueous phase comprising of Na$_2$CO$_3$ (0.1 M) and NaHCO$_3$ (0.1 M) in a ratio of 6 to 4 and an organic phase of CH$_2$Cl$_2$. The organic layer was collected and concentrated, sequentially, to provide a white cloudy solid in 86% yield (190 mg).

Anal. C$_{20}$H$_{24}$N$_2$O$_2$, MW=324.4, ESI+Q-TOF: M=324.2 (m/z), [M+H]$^+$=325.2; $^1$H-NMR (500 MHz, CD$_3$OD): δ 1.54-1.67 (m, 2H, aliphatic-H), 2.61 (t, J=6.5 Hz, 2H, aliphatic-H), 3.21 (t, J=6.5 Hz, 2H, aliphatic-H), 3.27-3.33 (m, 4H, aliphatic-H), 3.36 (t, J=6.5 Hz, 2H, aliphatic-H), 7.38 (dd, J=7.5 Hz, 1H, Ar—H), 7.46 (dd, 2H, Ar—H), 7.67 (d, J=7.0 Hz, 2H, Ar—H), 7.74 (d, J=6.5 Hz, 2H, Ar—H), 8.07 (d, J=6.5 Hz, 2H, Ar—H); $^{13}$C-NMR (125 MHz, CD$_3$OD): δ 27.26 (CH$_2$), 27.68 (CH$_2$), 30.81 (CH$_2$), 34.88 (CH$_2$), 39.84 (CH$_2$), 52.14 (CH$_2$), 127.43 (Ar, CH), 127.99 (Ar, CH), 128.07 (Ar, CH), 128.19 (Ar, CH), 128.57 (Ar—CH), 129.34 (Ar—CH), 129.79 (Ar, CH), 129.92 (Ar, CH), 130.07 (Ar—CH), 136.78 (Ar, C), 141.09 (Ar, C), 147.16 (Ar, C), 175.01 (HN—C=O, C), 200.31 (C=O, C).

methyl 4-(biphenyl-4-yl)-A-oxobutanoate (compound 7)

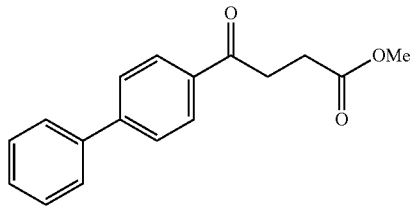

To a stirred solution of N-nitrosomethylurea (810 mg, 7.8 mmol) in Et$_2$O (150 ml) was add KOH (400 mg, 1.8 eq, 7.2 mmol) at 0° C. The pale yellow organic phase was partitioned with ice-cold H2O (100 mL) and the organic layer was collected, followed by washing with another portion of ice-cold aqueous KOH (2 N, 75 mL). The solution of Et$_2$O was slowly (50 mL/min) added to a two-necked round-bottomed flask containing 4-(biphenyl-4-yl)-4-oxobutanoic acid (1 g, 3.93 mmol) and EtOAc (100 mL) at 0° C. under Ar. The addition was terminated when the color turned yellow. TLC (EtOAc/n-hexane 1:7) indicated the consumption of the starting material 3 ($R_f$=0.12) and the formation of the product 7 ($R_f$=0.33). One drop of acetic acid was then added. After partition using saturated NaHCO$_3$ (aq), the organic layer was concentrated. The residue was purified by flash chromatography using eluents EtOAc/n-hexane 1:4 to provide white slices of crystallized product in 85% yield (896 mg).

Anal. C$_{17}$H$_{16}$O$_3$, MW=268.3, ESI+Q-TOF: M=268.1 (m/z), [M+H]$^+$=269.1; $^1$H-NMR (500 MHz, CDCl$_3$): δ 2.78 (t, J=7.0 Hz, 2H, aliphatic-CH$_2$), 3.34 (t, J=7.0 Hz, 2H, aliphatic-CH$_2$), 3.70 (s, 2H, OCH$_2$CO), 7.36-7.41 (m, 1H, Ar—H), 7.42-7.49 (m, 2H, Ar—H), 7.58-7.64 (m, 2H, Ar—H), 7.67 (d, J=9.0 Hz, 2H, Ar—H), 8.04 (d, J=8.5 Hz, 2H, Ar—H); $^{13}$C-NMR (125 MHz, CDCl$_3$): δ 27.82 (CH$_2$), 33.19 (CH$_2$), 51.60 (CH$_3$), 126.98 (Ar, CH), 127.01 (Ar, CH), 128.05 (Ar, CH), 128.42 (Ar, CH), 128.75 (Ar, CH), 134.99 (Ar, C), 139.52 (Ar, C), 145.56 (Ar, C), 173.15 (H$_3$COC=O, C), 197.39 (Ar—C=O—CH$_2$, C).

1-(4-((4-azidobutylaminooxy)methyl)-2,3-dichlorophenyl)-2-methylenebutan-one (compound 9)

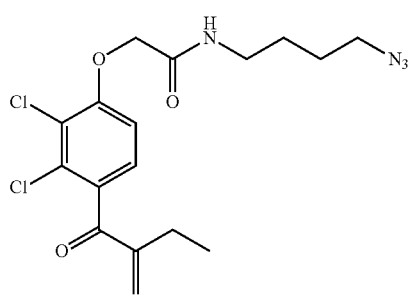

The same procedure as preparation for compound 4 was used. In addition to flash chromatography (acetone/n-hexane=¼), a partition between 1N HCl (10 mL) and CH$_2$Cl$_2$ (20 mL) to collect the organic layer was performed in advance. TLC (MeOH/CHCl$_3$=¼) indicated the consumption of starting material 8 ($R_f$=0.42) and the formation of the product 9 ($R_f$=0.88). The colorless oil was obtained in 86% yield (550 mg).

Anal. C$_{17}$H$_{20}$Cl$_2$N$_4$O$_3$, MW=399.3, ESI+Q-TOF: M=398.0, 400.0 (m/z), [M-N2+H]$^+$=371.04, 373.03 (3:2), equivalent to the calculated isotopic ratio; $^1$H-NMR (500 MHz, CDCl$_3$): δ 1.12 (t, J=8.0 Hz, 3H, CH$_3$), 1.62-1.71 (m, 4H, butyl-H), 2.44 (t, J=7.0 Hz, 2H, CH$_2$CH$_3$), 3.32 (t, J=6.0 Hz, 2H, butyl-H), 3.40 (q, J=6.5 Hz, 2H, butyl-H), 4.55 (s, 2H, OCH$_2$—C=O—NH), 5.56 (s, 1H, C=CH$_2$), 5.94 (s, 1H, C=CH$_2$), 6.80 (s, 1H, NH), 6.84 (d, 1H, Ar—H), 7.17 (d, 1H, Ar—H); $^{13}$C-NMR (125 MHz, CDCl$_3$): δ 12.35 (CH$_3$), 23.37 (CH$_2$), 26.17 (CH$_2$), 26.81 (CH$_2$), ?30.92 (CH$_3$), 38.55 (CH$_2$), 50.95 (CH$_2$), 68.14 (O—CH$_2$), 110.87 (Ar, CH), 127.23 (Ar, CH), 128.79 (C=C, CH$_2$), 134.21 (C=C, C), 150.15 (Ar, C), 154.41 (Ar, C), 166.77 (Ar, C), ?176.31 (Ar, C), ?195.52 (NH—C=O, C), 207.04 (C=O, C).

1-(4-((4-aminobutylaminooxy)methyl)-2,3-dichlorophenyl)-2-methylenebutan-1-one (compound 10)

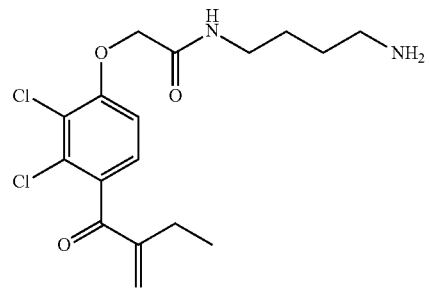

The same procedure as the preparation for compound 5 was used. TLC (MeOH/CHCl$_3$/NH$_{3(aq)}$=1/1/0.02) indicated the consumption of starting material 9 ($R_f$=0.95) and the formation of the product 10 ($R_f$=0.40). A mixture of starting material (199 mg, 0.5 mmol), Pd/C (20 mg) and MeOH (15 mL) was employed to provide a colorless oil in 80% yield (150 mg).

Anal. C$_{17}$H$_{22}$Cl$_2$N$_2$O$_3$, MW=373.3, ESI+Q-TOF: M=372.1, 374.1 (m/z), [M+H]$^+$=373.13, 375.14 (3:2), equivalent to the calculated isotopic ratio; $^1$H-NMR (500 MHz, CD$_3$OD): δ 1.14 (t, J=7.5 Hz, 3H, CH$_3$), 1.53-1.68 (m, 4H, butyl-CH$_2$), 2.44 (q, J=6.5 Hz, 2H, CH$_2$—CH$_3$), 3.28-3.35 (m, 4H, butyl-CH$_2$), 4.69 (s, 2H, O—CH$_2$—C=O—NH), 5.59 (s, H, C=CH$_2$), 6.03 (s, H, C=CH$_2$), 7.07 (d, J=9.0 Hz, 1H, Ar—H), 7.24 (d, J=8.5 Hz, 1H, Ar—H); $^{13}$C-NMR (125 MHz, CD$_3$OD): δ ?8.15 (CH$_3$), 12.96 (CH$_3$), 24.49 (CH$_2$), 27.23 (CH$_2$), 27.66 (CH$_2$), ?30.71 (CH$_3$), 39.62 (CH$_2$), 52.33 (O—CH$_2$), 69.75 (vinyl, CH$_2$), 112.81 (Ar, CH), 128.49 (Ar, CH), 130.00 (C=C, CH$_2$), 131.85 (C=C), 134.97 (Ar, C), 151.67 (Ar, C), 156.86 (Ar, C), 169.83 (Ar, C), 197.29 (HN—C=O, C), 210.22 (C=O, C).

N-(4-(4-(biphenyl-4-yl)-4-oxobutanamido)butyl)-5-(2,5-dimethylphenoxy)-2,2-dimethylpentanamide (compound 12)

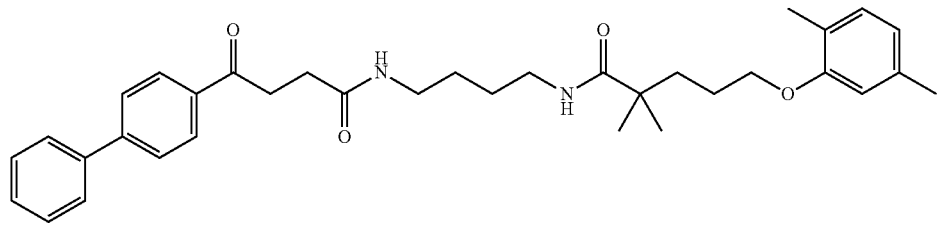

A mixture of Gemfibrozil (25 mg, 0.1 mmol), HBTU (37 mg, 0.1 mmol), DIEA (0.11 mL, 0.1 mmol) and DMF (15 mL) was stirred for 10 min. Compound 5 (35 mg, 0.1 mmol) was added. After 5 min, TLC (acetone/n-hexane=⅔) indicated the consumption of the starting material 5 ($R_f$=0.01) and the formation of the product 12 ($R_f$=0.42). The mixture was concentrated under high vacuum at 60° C. The residue was purified by flash chromatography using eluents MeOH: chloroform=1:19, followed by recrystallization using the combination of acetone and hexane to provide snow-white slices of solid in 81% yield (45 mg).

Anal. $C_{35}H_{44}N_2O_4$, MW=556.7, ESI+Q-TOF: M=556.3, 557.3, 558.3 (m/z), [M+H]$^+$=557.3; [M+Na]$^+$=579.3 (100%), 580.3 (38%), 581.3 (10%), equivalent to the calculated isotopic ratio; $^1$H-NMR (500 MHz, CDCl$_3$): δ 1.18 (s, 6H, CH$_3$), 1.53 (s, 4H, CH$_2$), 1.63-1.77 (m, 4H, CH$_2$), 2.14 (s, 3H, CH$_3$), 2.27 (s, 3H, CH$_3$), 2.63 (t, J=6.0 Hz, 2H, CH$_2$), 3.27 (br.s, 4H, CH$_2$), 3.38 (t, J=6.0 Hz, 2H, CH$_2$), 3.89 (t, J=6.0 Hz, 2H, CH$_2$), 5.93 (br.s, 1H, NH), 6.37 (br.s, 1H, NH), 6.58 (s, 1H, Ar—H), 6.63 (d, J=7.0 Hz, 1H, Ar—H), 6.97 (d, J=7.0 Hz, 1H, Ar—H), 7.38 (t, J=7.0 Hz, 1H, Ar—H), 7.45 (t, J=7.5 Hz, 2H, Ar—H), 7.59 (d, J=8.0 Hz, 2H, Ar—H), 7.65 (d, J=8.5 Hz, 2H, Ar—H), 8.02 (d, J=8.0 Hz, 2H, Ar—H); $^{13}$C-NMR (125 MHz, CDCl$_3$): δ 15.57 (CH$_3$), 15.79 (CH$_3$), ?20.00 (CH$_3$), 21.37 (CH$_3$), 25.12 (C$_{1-12}$), ?25.54 (CH$_3$), 26.36 (CH$_2$), 27.04 (CH$_2$), 30.01 (CH$_2$), 34.21 (CH$_2$), 37.47 (CH$_2$), 39.07 (CH$_2$), 39.50 (CH$_2$), 41.88 (C), 67.96 (CH$_2$), 112.12 (Ar, CH), 113.63 (Ar, CH), 120.80 (Ar, CH), 123.45 (Ar, C), 125.85 (Ar, CH), 127.07 (Ar, CH), 127.25 (Ar, CH), ?127.35 (Ar, CH), 128.28 (Ar, CH), 128.69 (Ar, CH), 128.95 (Ar, CH), 130.31 (Ar, CH), 130.54 (Ar, CH), 135.12 (Ar, C), 136.53 (Ar, C), 139.76 (Ar, C), 146.03 (Ar, C), 156.88 (Ar, C), 172.99 (HNC=O, C), 177.99 (HNC=O, C), 198.70 (C=O, C).

N-(4-(4-(biphenyl-4-yl)-4-oxobutanamido)butyl)-2-ethylhexanamide (compound 13)

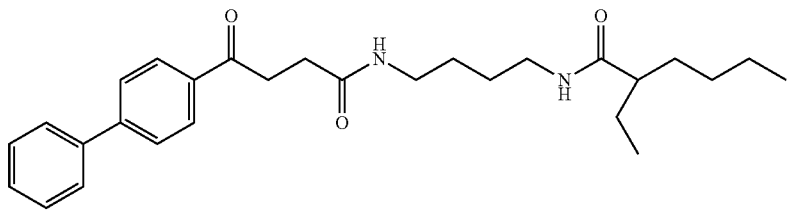

A mixture of 2-ethylhexanoic acid (38 μL, 1 mmol), HBTU (37 mg, 0.1 mmol), DIEA (0.11 mL, 0.1 mmol) and DMF (15 mL) was stirred for 10 min. Compound 5 (35 mg, 0.1 mmol) was added. After 5 min, TLC (acetone/n-hexane=¼) indicated the consumption of the starting material ($R_f$=0.01) and the formation of the product ($R_f$=0.33). The mixture was concentrated under high vacuum at 60° C. The residue was purified by flash chromatography using eluents acetone/hexane=¼, followed by precipitation using the combination of acetone and hexane to provide off-white solids in 55% yield (25 mg).

Anal. $C_{28}H_{38}N_2O_3$, MW=450.6, ESI+Q-TOF: M=450.3, 451.3, 452.3 (m/z), [M+H]*=451.3; [M+Na]*=473.3 (100%), 474.3 (33%), 475.3 (5.5%), equivalent to the calculated isotopic ratio; $^1$H-NMR (500 MHz, CDCl$_3$): δ 0.74-0.93 (m, 6H, CH$_3$), 1.12-1.32 (m, 4H, aliphatic-CH$_2$), 1.32-1.48 (m, 2H, aliphatic-CH$_2$), 1.50-1.69 (m, 6H, aliphatic-CH$_2$), 1.86-1.96 (m, 1H, CH), 2.63 (t, J=6.0 Hz, 2H, aliphatic-CH$_2$), 3.27 (br.s, 4H, aliphatic-CH$_2$), 3.38 (t, J=6.0 Hz, 2H, aliphatic-CH$_2$), 5.98 (br.s, 1H, NH), 6.29 (br.s, 1H, NH), 7.36-7.40 (m, 1H, Ar—H), 7.42-7.48 (m, 2H, Ar—H), 7.57-7.63 (m, 2H, Ar—H), 7.65 (d, J=8.0 Hz, 2H, Ar—H), 8.02 (d, J=8.5 Hz, 2H, Ar—H); $^{13}$C-NMR (125 MHz, CDCl$_3$): δ 12.10 (CH$_3$), 13.96 (CH$_3$), 22.69 (CH$_2$), 25.95 (CH$_2$), 26.71 (CH$_2$), 29.81 (CH$_2$), 30.18 (CH$_2$), 32.36 (CH$_2$), 34.13 (CH$_2$), 39.08 (CH$_2$), 39.21 (CH$_2$), 49.47 (aliphatic-CH), 127.24 (Ar, CH), 128.26 (Ar, CH), 128.65 (Ar, CH), 128.95 (Ar, CH), 135.19 (Ar, C), 139.75 (Ar, C), 145.98 (Ar, C), 172.78 (HNC=O, C), 176.75 (HNC=O, C), 198.68 (C=O, C).

4-(biphenyl-4-yl)-N-(4-(2-(2,3-dichloro-4-(2-methylenebutanoyl)phenoxy)acetamido)butyl)-4-oxobutanamide (compound 14)

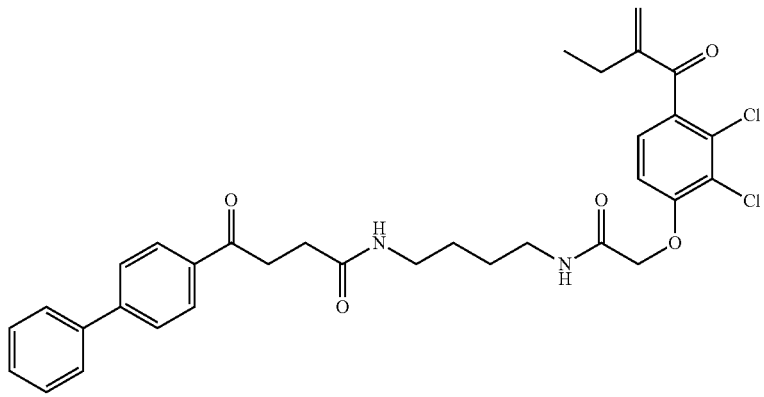

A mixture of the corresponding ethacrynic acid (13 mg, 0.05 mmol), HBTU (19 mg, 0.05 mmol), DIEA (0.06 mL, 0.05 mmol) and DMF. (9 mL) was stirred for 15 min. Compound 5 (20 mg, 0.05 mmol) was added. After 5 min, TLC (acetone/n-hexane=½) indicated the consumption of the starting material ($R_f$=0.01) and the formation of the product ($R_f$=0.28). The mixture was concentrated under high vacuum at 60° C. The residue was purified by flash chromatography using eluents acetone/hexane=½, followed by precipitation using the combination of acetone and hexane to provide white solids in 61% yield (37 mg).

Anal. $C_{33}H_{34}Cl_2N_2O_5$, MW=609.5, ESI+Q-TOF: M=608.2, 609.2; 610.2 (m/z), [M+H]$^+$=609.20 (14%), 610.2 (5.2%), 611.2 (9%); [M+Na]$^+$=631.2 (100%), 632.2 (37%), 633.2 (70%), equivalent to the calculated isotopic ratio; $^1$H-NMR (500 MHz, CDCl$_3$): δ 1.12 (t, J=7.0 Hz, 3H, CH$_3$), 1.55 (q, J=7.5 Hz, 2H, CH$_2$CH$_2$NH), 1.59 (q, J=7.5 Hz, 2H, CH$_2$CH$_2$NH), 2.40-2.48 (m, 2H, CH$_2$—CH$_3$), 2.64 (t, J=7.0 Hz, 2H, aliphatic-CH$_2$), 3.22-3.32 (m, 2H, CH$_2$), 3.34-3.48 (m, 4H, CH$_2$), 4.55 (s, 2H, OCH$_2$CO), 5.56 (s, 1H, vinyl), 5.90 (br.s, 1H, NH), 5.92 (s, 1H, vinyl), 6.23 (br.s, 1H, NH), 6.77-6.89 (m, 1H, Ar—H), 7.08-7.18 (m, 1H, Ar—H), 7.34-7.40 (m, 1H, Ar—H), 7.44 (t, J=7.5 Hz, 2H, Ar—H), 7.59 (d, J=8.0 Hz, 2H, Ar—H), 7.65 (d, J=8.5 Hz, 2H, Ar—H), 8.02 (d, J=8.0 Hz, 2H, Ar—H); $^{13}$C-NMR (125 MHz, CDCl$_3$): δ 12.37 (CH$_3$), 23.39 (CH$_2$), 26.77 (CH$_2$), 26.86 (CH$_2$), 29.68 (C, q), 30.33 (CH$_2$), 34:18 (CH$_2$), 38.77 (CH$_2$), 39.14 (CH$_2$), 68.21 (O—CH$_2$), 110.85 (Ar, CH), 110.98 (Ar, CH), 127.24 (Ar, CH), 128.26 (Ar, CH), 128.67 (Ar, CH), 128.83 (C=CH$_2$), 128.95 (Ar, CH), ?131.47 (Ar, C), ?133.94 (Ar, C), ?134.21 (Ar, C), 135.19 (Ar, C), 139.77 (Ar, C), 145.97 (Ar, C), 150.16 (Ar, C), 154.51 (Ar, C), 166.99 (Ar, C), 169.19 (HNC=O), 172.51 (HNC=O), 195.59 (C=O), 198.78 (C=O).

Example 2

Cytotoxicity Studies by MTT Assay

The cell lines were used in the present invention, including C26 (solid murine colon carcinoma), A549 (Human type II epithelial cell line, from American Type Culture Collection, Manassas, Va.), MCF7 (solid human estrogen receptor positive breast carcinoma) and Tramp C1 (transgenic adenocarcinoma of the mouse prostate).

10 μL combinatorial compound was added into the well of microtiterplate planted with 100 μL of abovementioned cell lines in a concentration of 30000 cells/mL. After an incubation of 2 days, the supernatants were washed, followed by adding MTT reagents. After 4 hrs, absorbance at 580 nm was recorded according to the usual protocol.

Figure 1B:
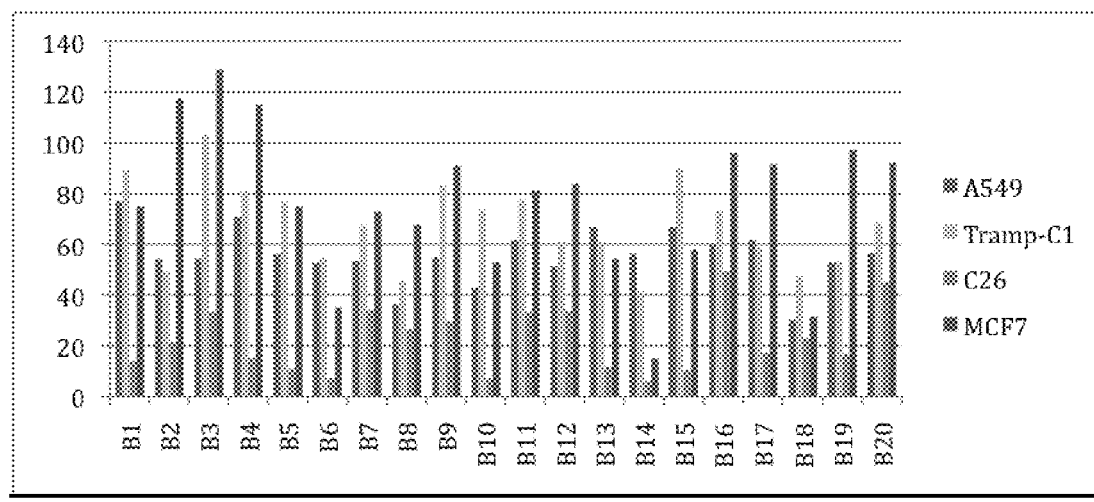
FIG. 1: Apparent survival ratio of the four cells treating with butylfenbufen analogs.
Figure 1C:
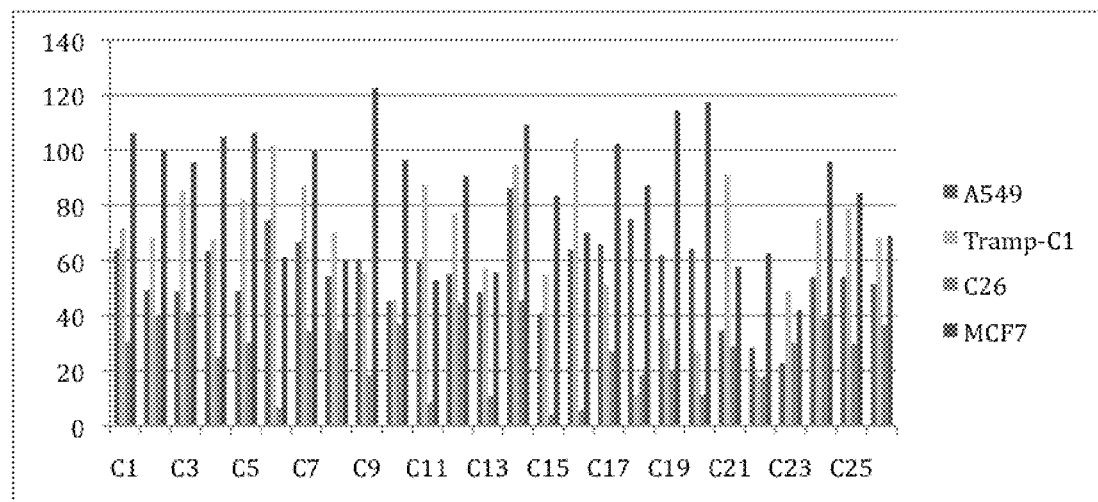
Figure 1D:
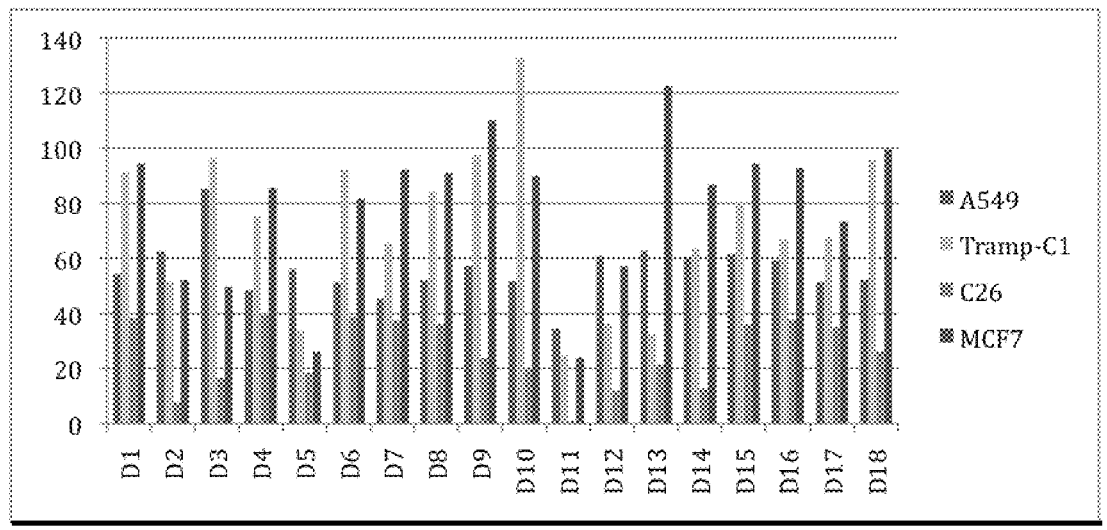
Figure 1E:
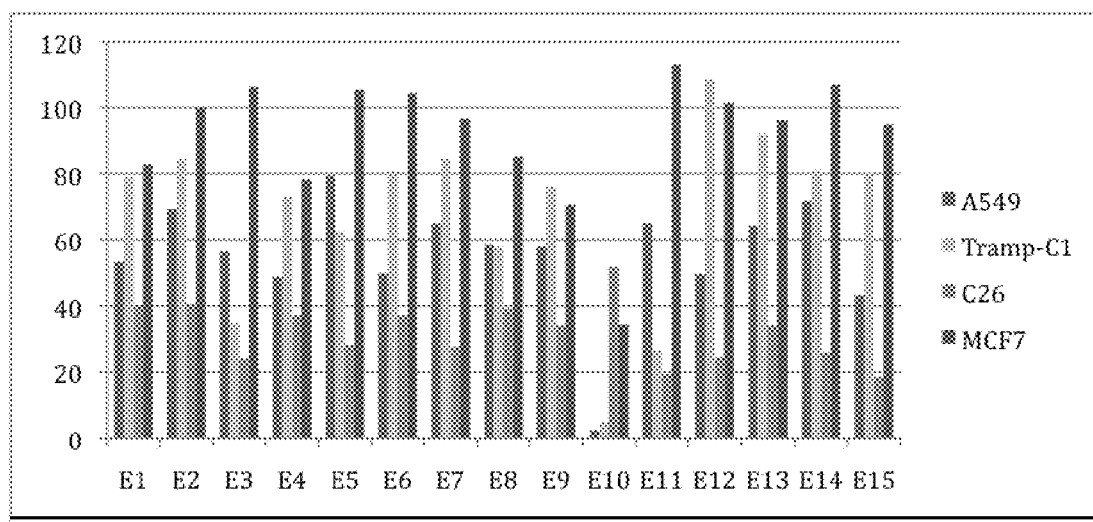
Figure 2A:
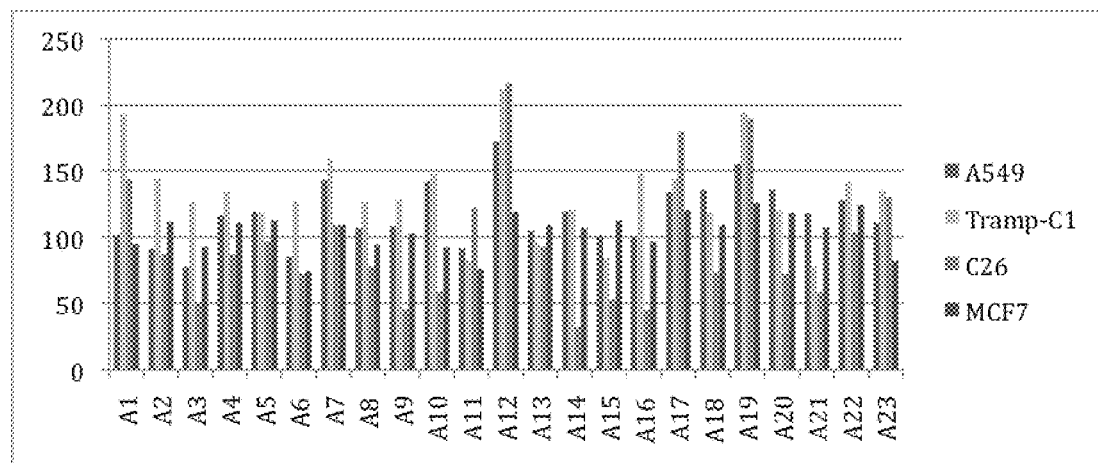
FIG. 2(A) mono-aromatic ring, FIG. 2(B) heteroaromatic, FIG. 2(C) aromatics containing halogen, FIG. 2(D) aliphatics and FIG. 2(E) aliphatic groups containing heteroatoms such as phosphor and aza acids.
Figure 2B:
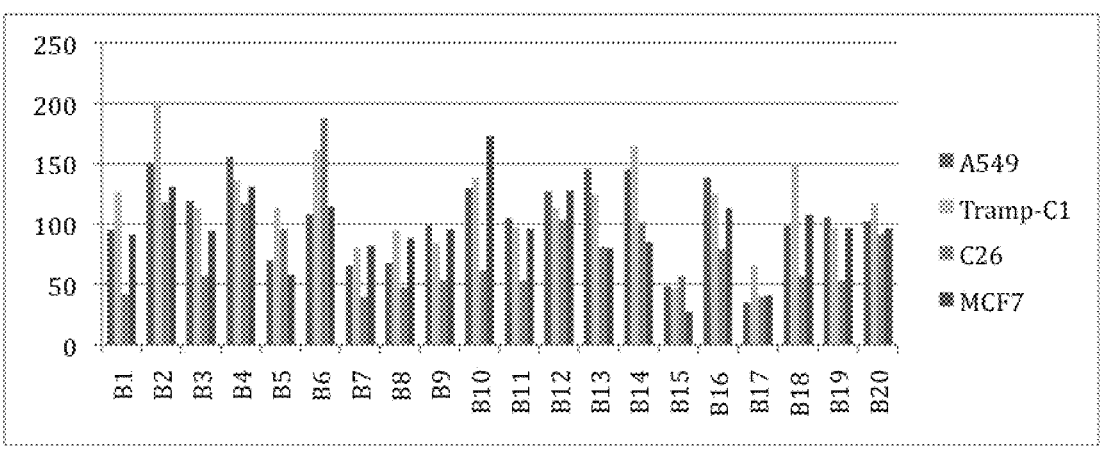
FIG. 2: Apparent survival ratio of the four cells treating with ethacrynic amide analogs.
Figure 2C:
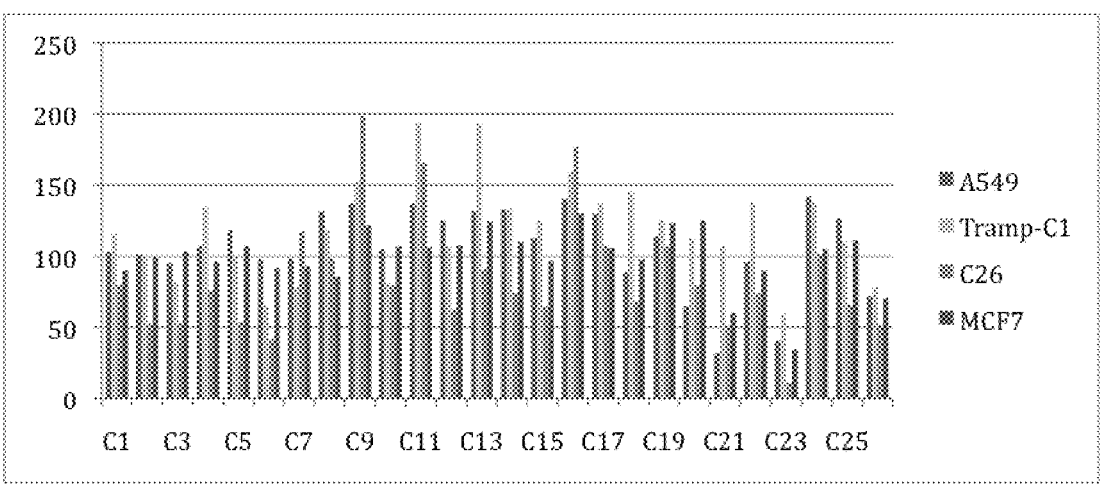
Figure 2D:
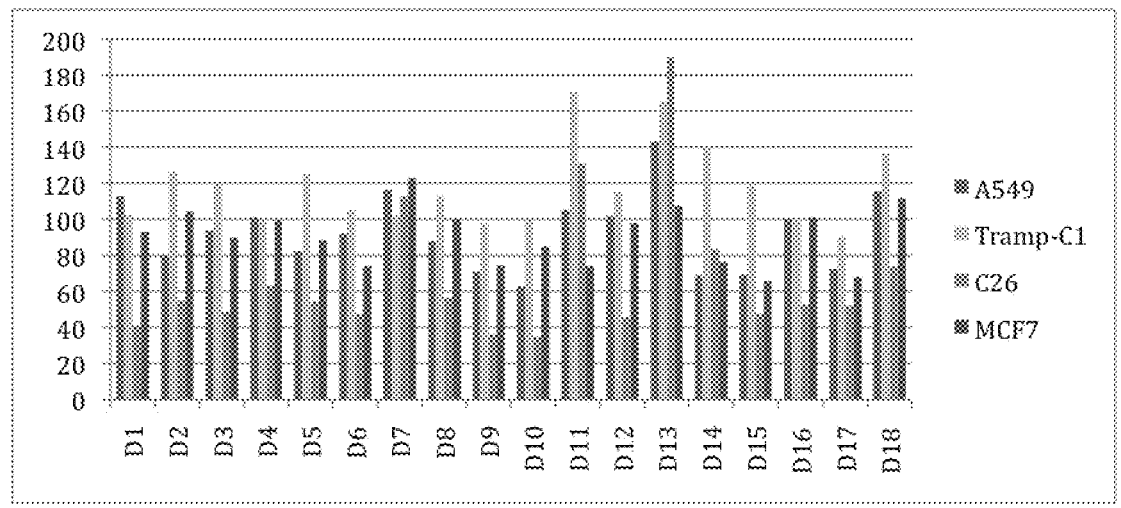
Figure 2E:
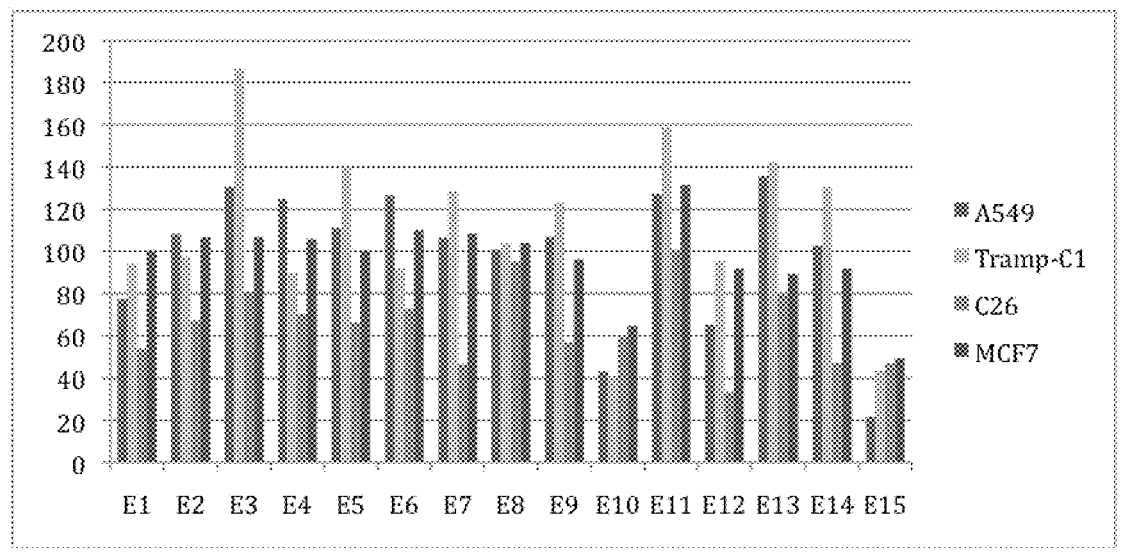

As shown in FIG. 1 and FIG. 2, the bioactivity trend is roughly related to the current arbiturary classification on structural basis. Consequently, it is needed to find a suitable classification to fulfill the structure and activity relationship (SAR) requirement.

According to the result of MTT assay, three compounds, N-(4-(4-(biphenyl-4-yl)-4-oxobutanamido)butyl)-5-(2,5-dimethylphenoxy)-2,2-dimethylpentanamide (1(W), compound 12), N-(4-(4-(biphenyl-4-yl)-4-oxobutanamido)butyl)-2-ethylhexanamide (4(E), compound 13) and 4-(biphenyl-4-yl)-N-(4-(2-(2,3-dichloro-4-(2-methylenebutanoyl)phenoxy)acetamido)butyl)-4-oxobutanamide (3(W), compound 14), were selected for the IC$_{50}$ test.

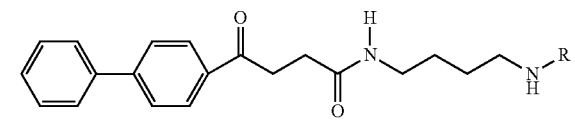

12, R = 1(W)
13, R = 4(E)
14, R = 3(W)

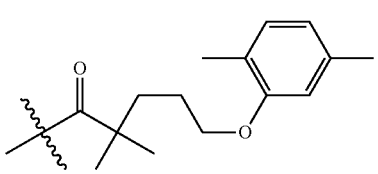

1(W)

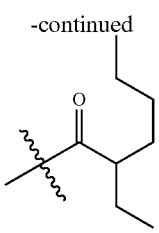

4(E)

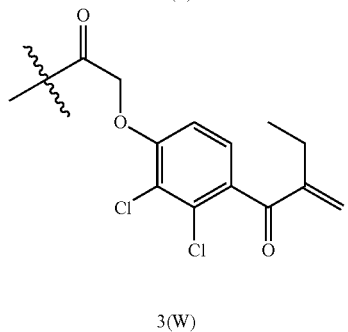

3(W)

As shown in Table 2, the three candidate compounds exerted comparable cytotoxicity profiles, except compound 14. Interestingly, compound 14 contained structural characteristics of both fenbufen and ethacrynic acid. But the void of cytotoxicity against Tramp C-1 cell may attribute to a lack of the expression of the corresponding receptor or a totally modified environment of its active site because of the gene transfection pretreatment.

TABLE 2

Inhibition of the potential compounds against the growth of sarcoma cells derived from human and murine

| Cells analyzed | IC50 values Cisplatin | compound 12 | compound 13 | compound 14 | Fenbufen |
|---|---|---|---|---|---|
| A549 | 15 | 9 | 17 | 19 | >100 |
| MCF7 | 10 | 2 | <1 | 5 | 10 |
| TRAMP C-1 | 22 | 21 | 18 | >100 | >100 |
| C26 | 17 | 15 | 15 | 35 | >100 |

The invention claimed is:

1. A compound of formula:

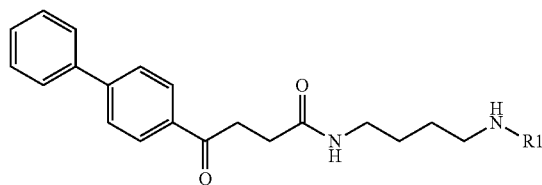

or

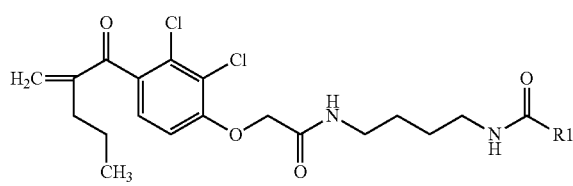

wherein the R1 represents substituted acyl wherein the acyl is substituted with an aromatic ring, heterocyclic ring, halo aromatic ring, aliphatic chain or heteroaliphatic chain.

2. The compound of claim 1, which is N-(4-(4-(biphenyl-4-yl)-4-oxobutanamido)butyl)-5-(2,5-dimethylphenoxy)-2,2-dimethylpentanamide, N-(4-(4-(biphenyl-4-yl)-4-oxobutanamido)butyl)-2-ethylhexanamide or 4-(biphenyl-4-yl)-N-(4-(2-(2,3-dichloro-4-(2-methylenebutanoyl)phenoxy)acetamido)butyl)-4-oxobutanamide.

3. A method for inducing cytotoxicity in a cancer cell comprising administering a subject the compound of claim 1.

4. The method of claim 3, wherein the subject is a cell, a tissue or a mammal.

5. The method of claim 3, wherein the compound is N-(4-(4-(biphenyl-4-yl)-4-oxobutanamido)butyl)-5-(2,5-dimethylphenoxy)-2,2-dimethylpentanamide, N-(4-(4-(biphenyl-4-yl)-4-oxobutanamido)butyl)-2-ethylhexanamide or 4-(biphenyl-4-yl)-N-(4-(2-(2,3-dichloro-4-(2-methylenebutanoyl)phenoxy)acetamido)butyl)-4-oxobutanamide.

6. A method for inhibiting the proliferation of tumor cells comprising administering to said tumor cells an inhibitory amount of the compound of claim 1.

7. The method of claim 6, wherein the tumor cell is colon carcinoma, epithelial carcinoma, breast carcinoma or prostate cancer cell.

8. The method of claim 6, wherein the compound is N-(4-(4-(biphenyl-4-yl)-4-oxobutanamido)butyl)-5-(2,5-dimethylphenoxy)-2,2-dimethylpentanamide, N-(4-(4-(biphenyl-4-yl)-4-oxobutanamido)butyl)-2-ethylhexanamide or 4-(biphenyl-4-yl)-N-(4-(2-(2,3-dichloro-4-(2-methylenebutanoyl)phenoxy)acetamido)butyl)-4-oxobutanamide.

9. A library of compounds comprising a of compound of formula:

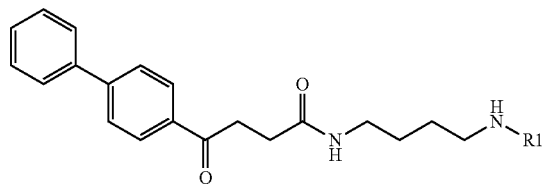

or

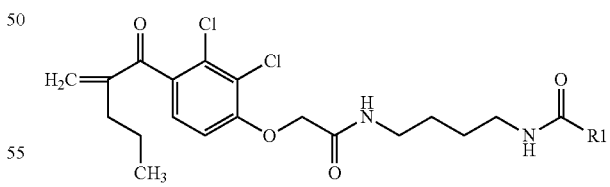

wherein the R1 represents

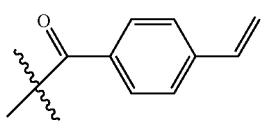

1(A)

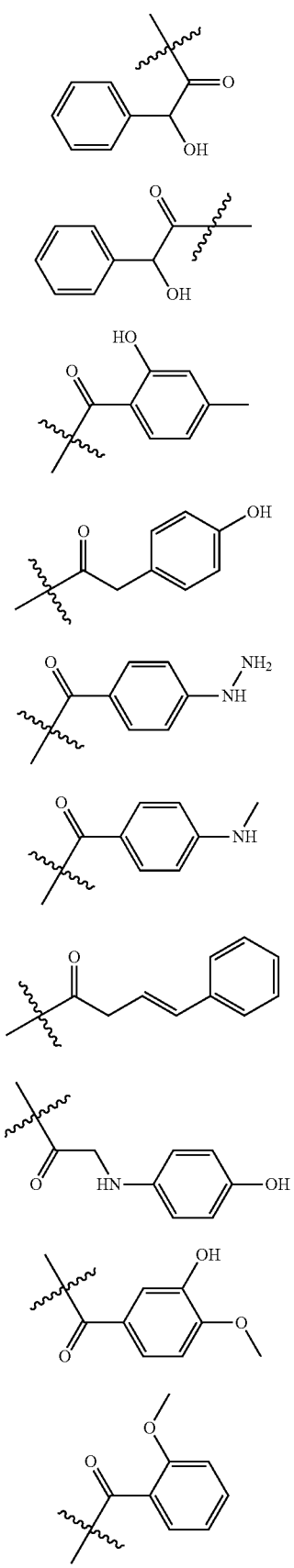
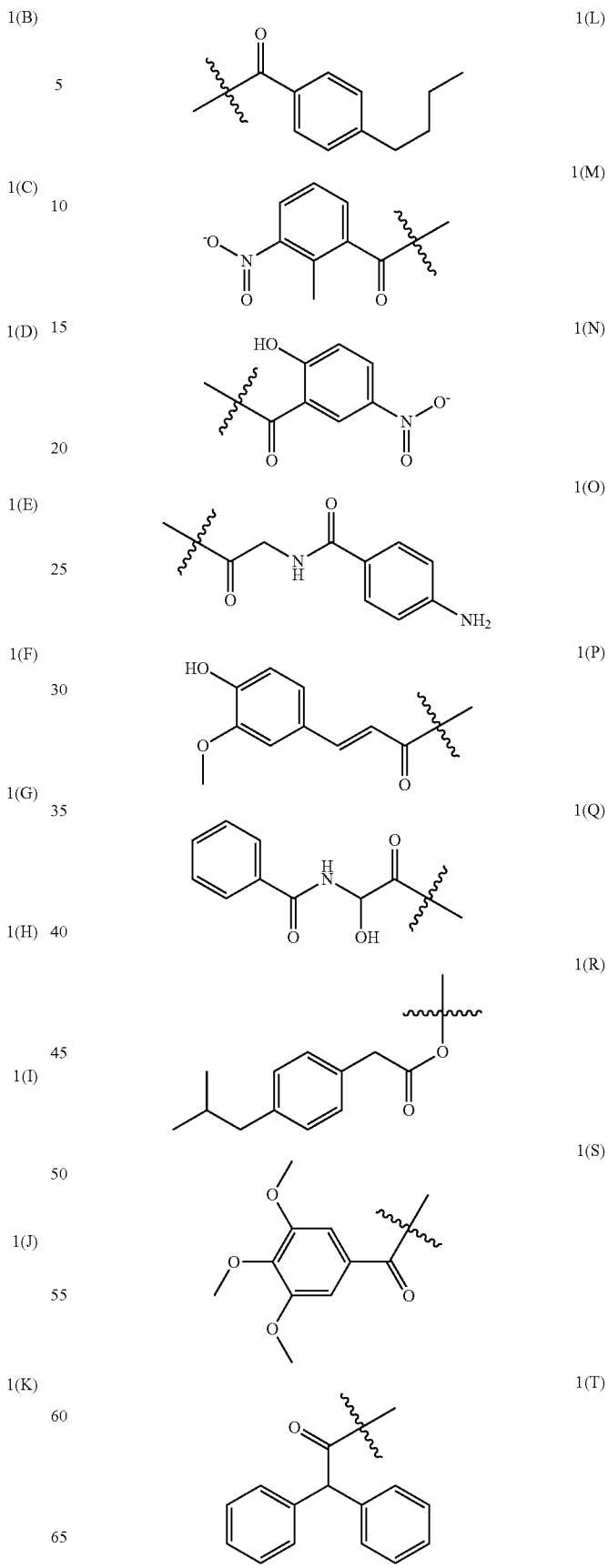

1(U) 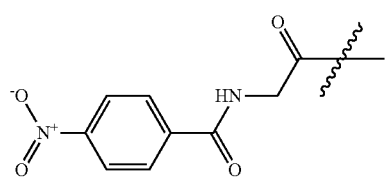
1(V) 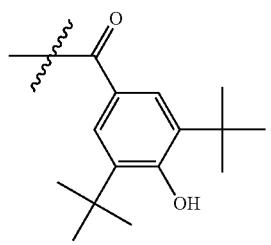
1(W) 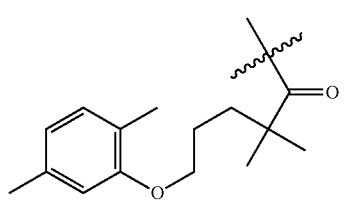
2(A) 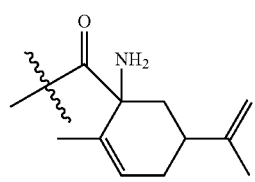
2(B) 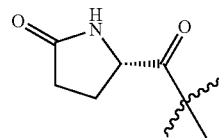
2(C) 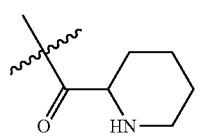
2(D) 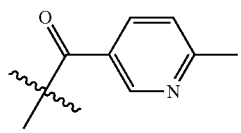
2(E) 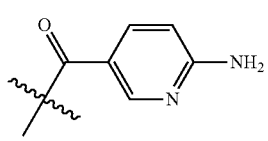
2(F) 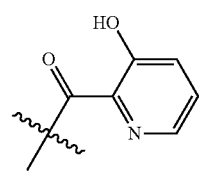
2(G) 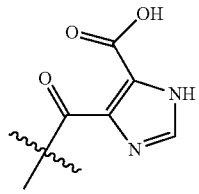
2(H) 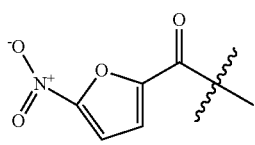
2(I) 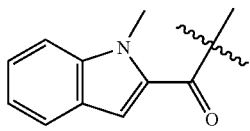
2(J) 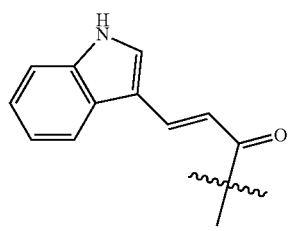
2(K) 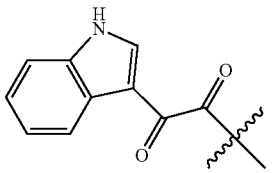
2(L) 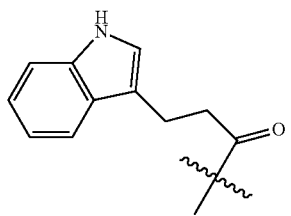
2(M) 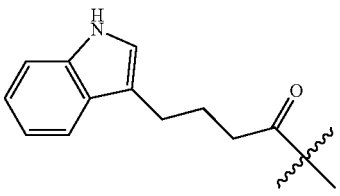
2(N) 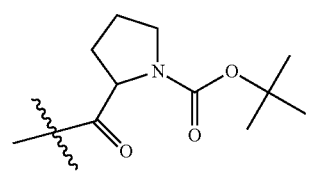

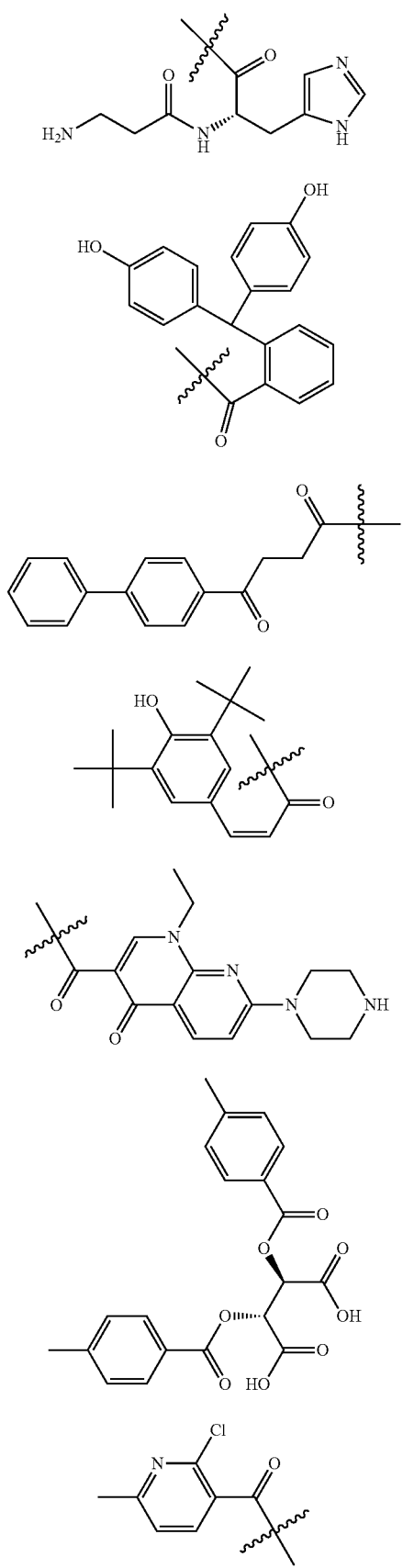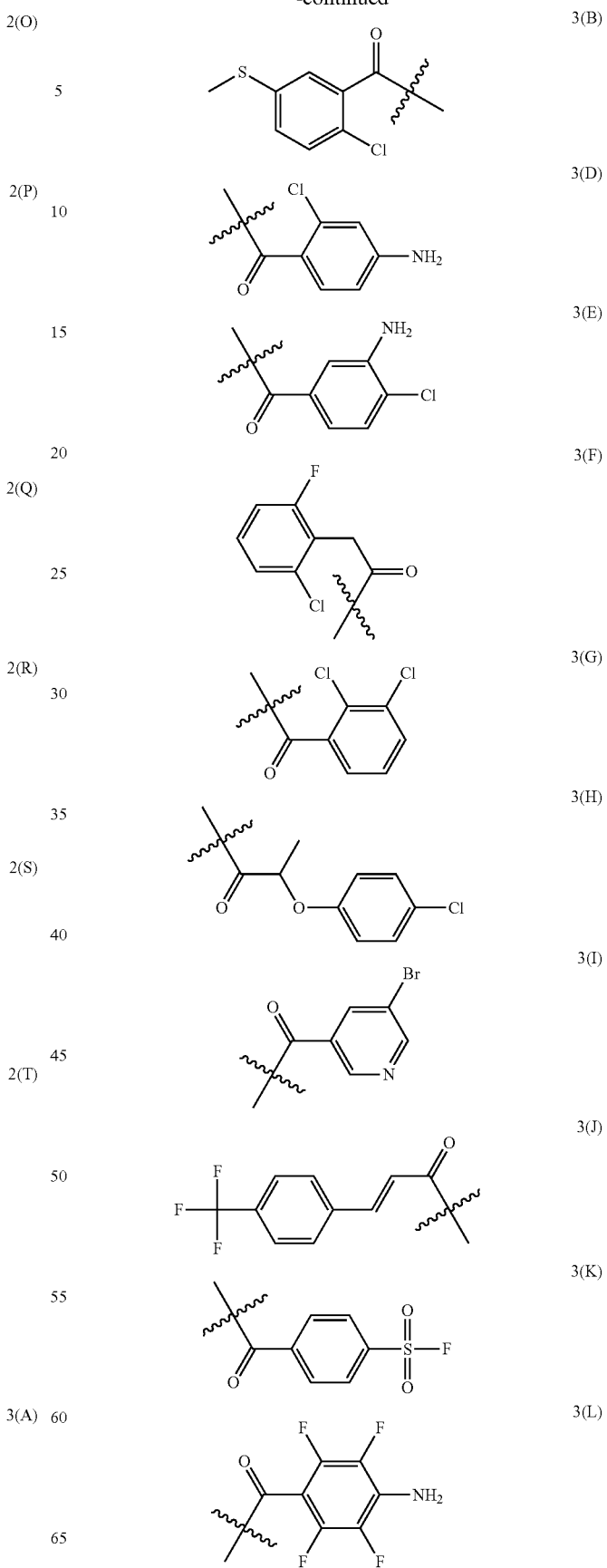

3(M)
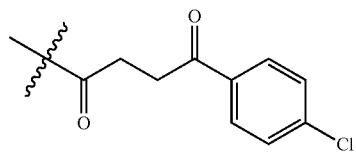
3(N)
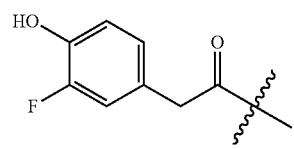
3(O)
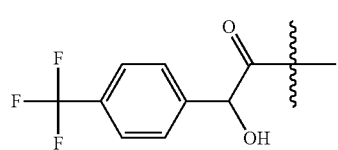
3(P)
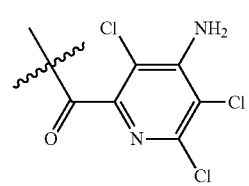
3(Q)
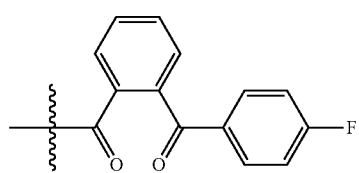
3(R)
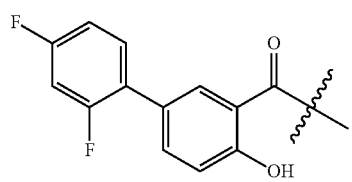
3(S)
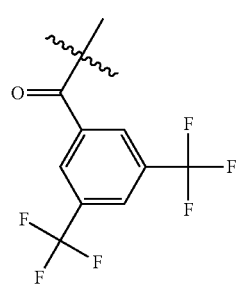
3(T)
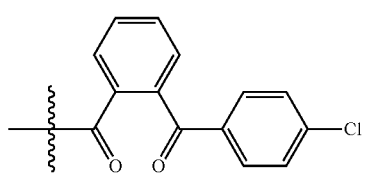
3(U)
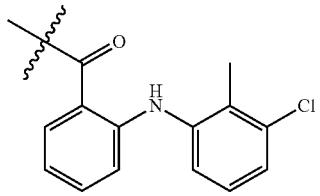
3(V)
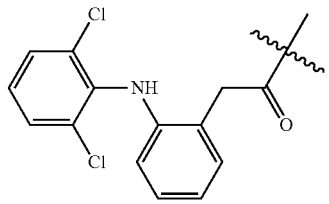
3(W)
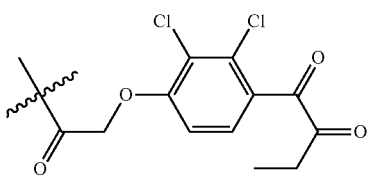
3(X)
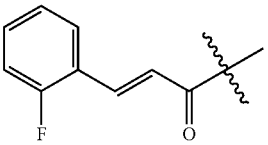
3(Y)
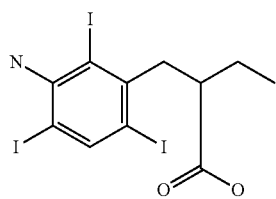
3(Z)
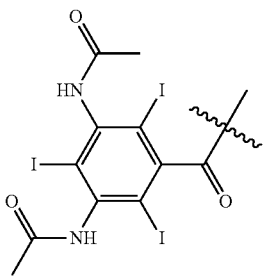
4(A)
4(B)
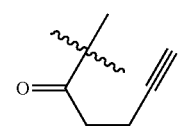

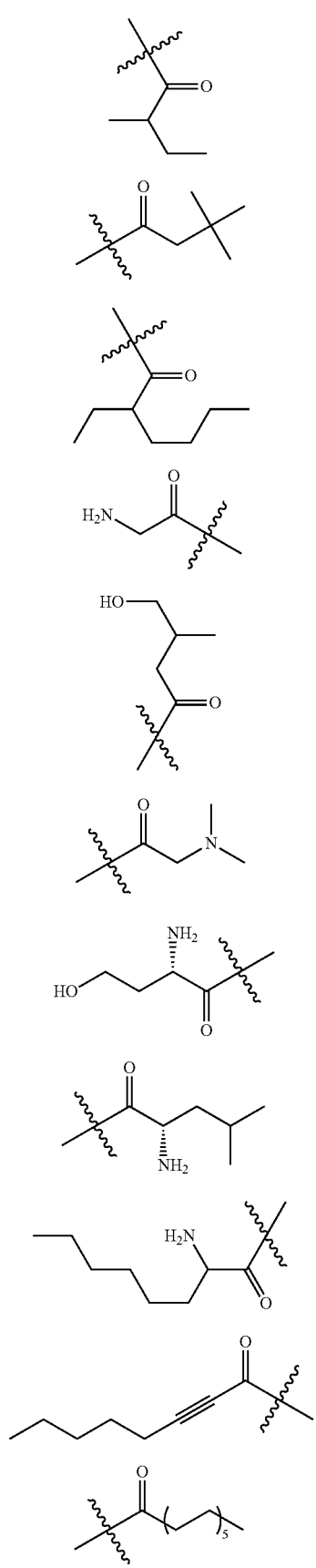
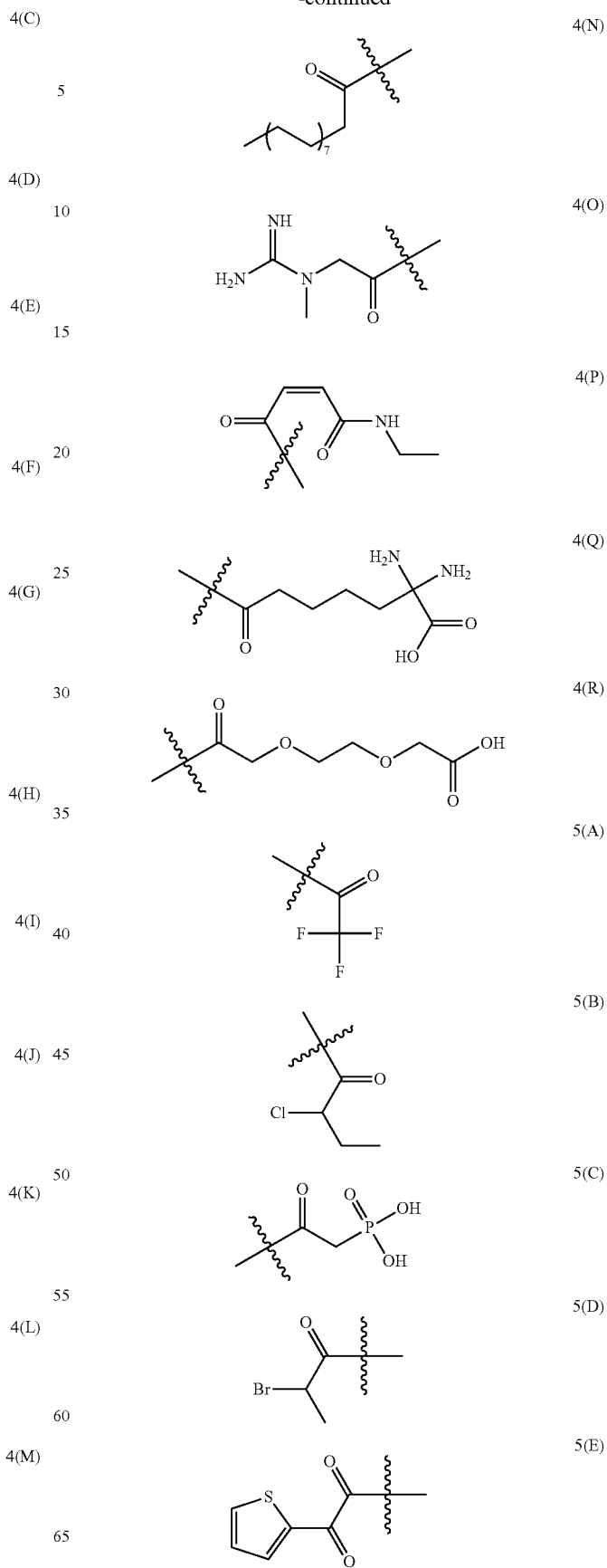

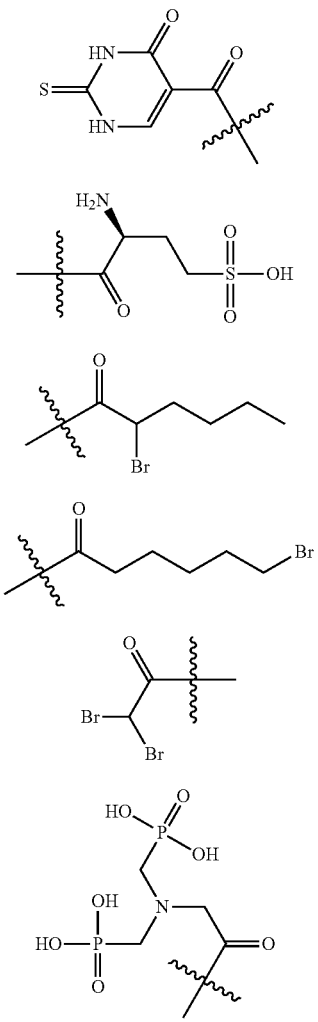
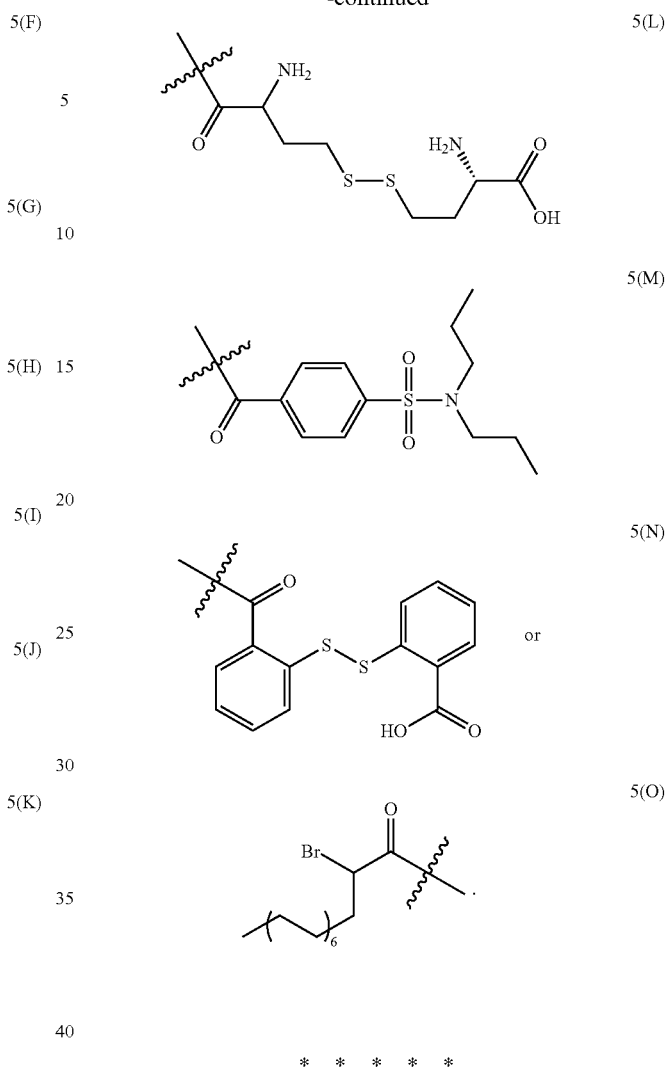
* * * * *